United States Patent
Serhan et al.

(10) Patent No.: US 6,416,965 B2
(45) Date of Patent: Jul. 9, 2002

(54) SCREENING METHODS FOR PRESQUALENE DISPHOSPHATE ANALOGS

(75) Inventors: Charles N. Serhan, Wellesley; Bruce D. Levy, West Roxbury, both of MA (US)

(73) Assignee: Brigham and Women's Hospital, Boston, MA (US)

( * ) Notice: Subject to any disclaimer, the term of this patent is extended or adjusted under 35 U.S.C. 154(b) by 0 days.

(21) Appl. No.: 09/736,005

(22) Filed: Dec. 13, 2000

Related U.S. Application Data

(63) Continuation of application No. 09/539,591, filed on Mar. 31, 2000, now Pat. No. 6,251,622, which is a continuation of application No. 09/055,592, filed on Apr. 6, 1998, now Pat. No. 6,066,466, which is a continuation-in-part of application No. 08/832,952, filed on Apr. 4, 1997, now Pat. No. 6,008,205.

(51) Int. Cl.$^7$ ............................................... C12Q 1/34
(52) U.S. Cl. ........................................ 435/18; 435/25
(58) Field of Search .................................... 435/18, 25

(56) References Cited

U.S. PATENT DOCUMENTS

| | | | | |
|---|---|---|---|---|
| 5,859,222 A | | 1/1999 | Leung et al. | 536/23.2 |
| 5,929,081 A | * | 7/1999 | Brown et al. | 514/263 |
| 6,008,205 A | * | 12/1999 | Serhan et al. | 514/102 |
| 6,066,466 A | * | 5/2000 | Serhan et al. | 435/18 |
| 6,251,622 B1 | * | 6/2001 | Serhan et al. | 435/18 |

OTHER PUBLICATIONS

V. Jo Davisson et al., "Negative Ion Fast AtomBombardment Mass Spectrometry of Isoprenoid Diphosphates and Related Analogs", *Bioorganic Chemistry*, vol. 16, No. 2, Jun. 1988, pp. 111–123.

C. Dale Poulter et al., "Squalene Synthetase. Inhibition by Ammonium Analogues of Carboncationic Intermediates in the Conversion of Presqualene Diphosphate to Squalene", *Journal of the American Chemical Society*, vol. 111, No. 10, May 1989, pp. 3734–3739.

L. J. Altman et al., "Studies in Terpene Biosynthesis. Synthesis and Resolution of Presqualene and Prephytoene Alcohols", *Journal of The American Chemical Society*, vol. 100, No. 19, Sep. 1978, pp. 6174–6182.

H.C. Rilling et al., "Studies on the Mechanism of Squalene Biosynthesis. Presqualene, a Pyrophosphorylated Precursor to Squalene", *Journal of the American Chemical Society*, vol. 91, No. 4, Feb. 1969, pp. 1041–1042.

Abousalham, A.., et al., "Improved Purification and Biochemical Characterization of Phospholipase D. From Cabbage" Biochemica et Biophysica Acta 1158:1–7 (1993).

Adair, W. L., et al., Isolation and Assay of Dolichol and Dolichyl Phosphate: Methods in Enzymology 111:201–215 (1985).

Agwu, D.E., et al., "Phosphatidic Acid as a Second Messenger in Human Polymorphonuclear Leukocytes", J. Clin, Invest. 88:531–539 (1991).

Bagglioni, M., et al., "Activation of Neutrophil Leukocytes: Chemoattractant Receptors and Respiratory Burst" FASEB 7:1004–1010 (1993).

Berge, S.M., et al., "Pharmaceutical Salts" J. Pharm. Sciences vol. 66, No. 1: 1–19 (Jan./1977).

Bromberg, Y., et al., "Unsaturated Fatty Acids Stimulate NADPH–Dependent Superoxide Production by Cell–Free System Derived from Macrophages" Cellular Immunology, 88: 213–221 (1984).

Chen, P.S., et al., "Microdetermination of Phosphorus" Analytical Chemistry, vol. 28, No. 11:1756–1758 (Nov./1956).

Coates, R.M., et al., "Stereoselective Total Synthesis of Presqualene Alcohol", J. Amer. Chem. Soc., 93:1785–1786 (1971).

Cohen, L.H., et al., "Different Analogues of Farnesyl Pyrophosphate Inhibit Squalene Synthase and Protein: Farnesyltransferase to Different Extents", Biochem. Pharmcola., vol. 49, No. 6, 839–845 (1995).

Cornforth, R.H., et al., "Chemical Synthesis of Substrates of Sterol Biosynthesis" Methods, Enzymol. (Colowick, S.P. ed.) 15:359–390 (1969).

Corey, E.J., et al., "Application of Unreactive Analogs of Terpenoid Pyrophosphates to Studies of Multistep Biosynthesis, Demonstration that 'Presqualene Pyrophosphate' is an Essential Intermediate on the Path to Squalene", J. Amer. Chem. Soc., vol. 98, No. 5, 1291–1293 (1975).

Dillon, S.B., et al., "Regulation of Inositol Phosphate Metabolism in Chemoattractant–stimulated Human Polymorphonuclear Leukocytes", J. Biol. Chem., vol. 262, No. 25, 11546–11552 (1987).

Epstein, W.W., et al., "Studies on the Mechanism of Squalene Biosynthesis", J. Bio. Chem., vol. 245, No. 18, 4597–1605 (1970).

(List continued on next page.)

Primary Examiner—R Gitomer
(74) Attorney, Agent, or Firm—Dorsey & Whitney LLP; Scott D. Rothenberger

(57) ABSTRACT

The present invention is directed to presqualene diphosphate (PSDP) analogs having an active region of natural PSDP and a metabolic transformation region resistant to rapid intracellular inactivation in vivo. For example, PSDP and its stable analogs can inhibit neutrophil signal transduction events in cellular activation that result in the generation of active oxygen species, regulation of leukocyte adherence, both homotypic (leukocyte—leukocyte) or heterotypic adherence with leukocytes and epithelial cells of mucosal origin or endothelial cells of vascular origin. These analogs can also be used to regulate leukocyte-dependent tissue injury.

12 Claims, 18 Drawing Sheets

OTHER PUBLICATIONS

Exton, J.H., "Regulation of Phosphoinositide Phospholipases by Hormones, Neurotransmitters, and Other Agonists Linked to G. Proteins" Annu. Rev. Pharmacol. Toxicol., vol. 36, 481–508 (1996).

Farnsworth, C.C. et al., "Identification of Geranylgeranyl–Modified Proteins in HeLa Cells", Science 247: 320–322 (1990).

Fiore, S. et al., "Evaluation of Synthetic Sphingosine, Lysosphingolipids and Glycosphingolipids as Inhibitors of Functional Responses of Human Neutrophils" Biochem. J., 266: 25–31 (1990).

Goldstein, J.L., et al., "Regulation of the Mevalonate Pathway", Nature 343: 425–430 (1990).

Gomez–Cambronero, J., et al. "Granulocyte–Macrophage Colony–Stimulating Factor and the Neutrophil: Mechanisms of Action", *Cell–Cell Interactions in the Release of Inflammatory Mediators* (eds. Wong, P.Y–K and Serhan, C.N., Plenum Press, New York):35–71 (1991).

Goody, R.S., et al., "Thiophosphate Analogs of Nucleoside Di–and Triophosphate", J. Amer. Chem. Soc., vol. 93, No. 23, 6252–6257 (1971).

House, H., et al., "Preparation and Decomposition of Unsaturated Esters of Diazoacetic Acid", J. Org. Chem., vol. 33, No. 1, 53–60 (1968).

Jarstfer, M.B., et al., "Biosynthesis of Squalene: Evidence for a tertiary Cyclopropylcarbinyl Cationic Intermediate in the Rerrangement of) Presqualene Diphosphate To Squalene", J. Am. Chem. Soc., 118: 13089–13090 (1996.

Levy, B.D., et al., "Polyisoprenyl Phosphates in Intracellular Signaling", Nature, 389: 985–990 (1997).

Lowenstein, E.J., "The SH2 and SH3 Domain–Containing Protein GRB2 Links Receptor Tyrosine Kinases to ras Signaling" Cell, 70:431 (1992).

McPhail, L.C., et al., "Activation of the Respiratory Burst Enzyme from Human Neutrophils in a Cell–Free System", J. Clin. Invest. 75: 1735–1739 (1985).

McPhail, L.C., "SH3–dependent Assembly of the Phagocyte NADPH Oxidase", Journal of Experimental Medicine 180: 2011– (1994).

Mookhtiar, K.A., et al., "Yeast Squalene Synthase: A Mechanism for Addition of Substrates and Activation by NADPH", The Journal of Biological Chemistry, 269(15): 11201–11207 (1994).

Ortiz de Montellano, P. R., et al., "Substrate Selectivity of Squalene Synthetase", Biochemistry 16(12): 2680–2685 (1977).

Pawson, T., et al., "SH2 and SH3 Domains" Current Biology, 3:434– (1993).

Philips, M.R., et al., "Carboxyl Methylation of Ras–Related Proteins During Signal Transduction in Neutrophils", Science 259: 977–980 (1992).

Popjak, G. et al., "Biosynthesis and Structure of a New Intermediate Between Farnesyl Pyrophosphate and Squalene", The Journal of Biological Chemistry, 244(7): 1897–1918 (1969).

Poulter, C.D., et al., "Conversion of Farnesyl Pyrophosphate to Squalene", *Biosynthesis of Isoprenoid Compounds,* vol. 1, (eds. J.W. Porter and S.L. Spurgeon):ch. 8, 414–441 (1981).

Rhee, S.G., et al., "Regulation of Phosphoinositide–specific Phospholipase C Isozymes", Journal of Biological Chemistry, 272: 15045– (1997).

Stechter, I, et al., "A Deficiency of Mixed Function Oxidase Activities in the Cholesterol Biosynthetic Pathway of Human Granulocytes", Journal of Lipid Research, 21: 277–283 (1980).

Scheer, A., et al., "S–Prenylated Cysteine Analogues inhibit Receptor–Mediated G Protein Activation in Native Human Granulocyte and) Reconstituted Bovine Retinal Rod Outer Segment Membranes", Biochemistry 34: 4952–4961 (1995.

Serhan, C.N., et al., "Lipid Mediator Networks in Cell Signaling: Update and Impact of Cytokines", The FASEB Journal, 10: 1147–1158 (1996).

Silverman, R.B., "Prodrugs and Drug Delivery Systems", *The Organic Chemistry of Drug Design and Drug Action,* (Academic Press, Inc., San Diego, California): ch. 8, 352–401 (1992).

Takata, S., et al., "Remodeling of Neutrophil Phospholipids with 15(s)–Hydroxyeicosatetraenoic Acid Inhibits Leukotriene B4–induced Neutrophil Migration Across Endothelium", J. Clin. Invest., 93: 499– (1984).

Tou, J.S., et al., "Leukotriene B4 Stimulation of an Early Evelation of Phosphatidic Acid Mass in Human Neutrophils", Lipids 30(5): 373–381 (1995).

Van Dessel, G.A..F., "Dolichols and Dolichyl Derivatives" *CRC Handbook of Chromatography* (eds. Mukherjee, K.D., et al., CRC Press, Inc., Boca Raton): ch. 22, 321–377 (1993).

Weissmann, G., et al., "Release of Inflammatory Mediators From Stimulated Neutrophils" N.E. J. of Med., vol. 303, No. 1, 27–34 (Jul. 3, 1980).

Welbourn, C.R.B., et al., "Pathophysiology of Ischaemia Reperfusion Injury: Central Role of the Neutrophil", Br. J. Surg., 78: 651–655 (1991).

Imamura S., "Enzymatic Determination of Phospholipase D Activity with Choline Oxidase", J. Biochem. 83: 677–680 (1978).

* cited by examiner

| COMPOUND (#) | INORGANIC PHOSPHORUS (nmoles) | DENSITY ON TLC (ARBITRARY UNITS) | PHOSPHORUS / DENSITY |
|---|---|---|---|
| VI | 8.77 | 1.75 | 5.01 |
| VII | 4.10 | 1.52 | 2.70 |
| VIII | 7.34 | 2.80 | 2.62 |

INORGANIC PHOSPHORUS / SCANNING DENSITOMETRY: COMPOUND VI / COMPOUND VII = 1.86
COMPOUND VI / COMPOUND VIII = 1.91

THESE RATIOS INDICATE THAT: a) COMPOUND VI IS A *DI*PHOSPHATE, AND
b) COMPOUND VII & VIII ARE *MONO*PHOSPHATES.

*FIG. 1G*

| PMN LIPID | TLC[1]: Rf/DOL-P Rf | GC/MS[2]: DIRECT INJECTION | OTMS DERIVATIVE | ACID HYDROLYSIS TO SQUALENE | PHOSPHORUS[3]: nmoles/10[7] PMN | PROPOSED STRUCTURE: |
|---|---|---|---|---|---|---|
| COMPOUND V | 0.14 (±0.02) | 4.39 MIN: 235, 327, 261, 232, 220, 205, 189, 177, 91, 69 | NP | – | 0.11 (±0.04) | FARNESYL-DIPHOSPHATE * |
| COMPOUND VI | 0.25 (±0.02) | 8.81 MIN: 489, 447, 410, 341, 273, 205, 191, 136, 95, 81, 69 | 9.28 MIN: 486, 441, 405, 361 | + | 1.67 (±0.32) | PRESQUALENE-DIPHOSPHATE |
| COMPOUND VII | 0.44 (±0.03) | NP | 5.72 MIN: 356, 341, 313, 281, 207, 191, 145, 117, 97, 73, 69 | – | 0.35 (±0.13) | FARNESYL-MONOPHOSPHATE * |
| COMPOUND VIII | 0.66 (±0.04) | 8.81 MIN: 481, 403, 342, 268, 177, 136, 95, 81, 69 | 9.15 MIN: 486, 441, 403, 361 | – | 0,47 (±0.12) | PRESQUALENE-MONOPHOSPHATE |

*FIG. 2E*

PSDP (COMPOUND VI)
- INHIBITION OF $O_2^-$ GENERATION
- INHIBITION OF HOMOTYPIC ADHESION
- INHIBITION OF $IP_3$ INFORMATION

PMN RECEPTOR ACTIVATION →

PSMP (COMPOUND VIII)
INACTIVE

SCREENING METHODS FOR PRESQUALENE DISPHOSPHATE ANALOGS

RELATED APPLICATION

This application is a Continuation application of U.S. application Ser. No. 09/539,591, filed Mar. 31, 2000 now U.S. Pat. No. 6,251,622 which is a Continuation application of U.S. application Ser. No. 09/055,592 now U.S. Pat. No. 6,066,466, filed Apr. 6, 1998 which is a Continuation-in-Part application of U.S. application Ser. No. 08/832,952, filed on Apr. 4, 1997 now U.S. Pat. No. 6,008,205, the contents of which are hereby expressly incorporated herein by reference.

BACKGROUND OF THE INVENTION

The environment contains a variety of infectious microbial agents, such as viruses, bacteria, fungi and parasites, any one of which can cause pathological damage to the host organism. Consequently, most organisms, such as mammals, i.e. humans, have developed an immune system. The immune system is divided into two functional divisions, the innate immune system and the adaptive immune system.

The innate and adaptive immune systems consists of a variety of molecules and cells distributed throughout the body. The most important cells are leukocytes. Leukocytes are categorized as phagocytes, including polymorphonuclear neutrophils (PMNs), monocytes and macrophages, and lymphocytes, which mediate adaptive immunity.

Inflammation is the body's response to invasion or an injury, such as an invasion by an infectious microbial agent and includes three broad actions. First, the blood supply is increased to the area. Second, capillary permeability is increased, thereby permitting larger molecules to reach the site of infection. Third, leukocytes, particularly PMNs, migrate out of the capillaries and into the surrounding tissue. Once in the tissue, the PMNs migrate to the site of infection or injury by chemotaxis. These events manifest themselves as inflammation. Examples of conditions which cause these reactions to occur include clamping or tourniquet vessel-induced ischemia reperfusion injury, chronic inflammatory conditions such as asthma, rheumatoid arthritis, and inflammatory bowel disease, as well as autoimmune diseases.

Aberrant activation of phagocytic cells, in particular neutrophils, leads to the generation of superoxide anion, which when released to the extracellular milieu can evoke damage to surrounding tissues. Reactive oxygen species derived from neutrophil oxygen burst can play a deleterious role in generating secondary products that lead to loss of function. During surgery, in particular clamping of vessels, there is clear evidence that reperfusion following the release of the clamp involves neutrophil-derived mediators. The neutrophil-derived oxygen radicals and other toxic products that are normally intended for killing of microbial agents once they spill over into the surrounding tissue can lead to second organ injury, most notably in the lung and cardiac tissues, sequelae which are observed following ischemia reperfusion injury (Welbourn et al., *Brit. J. Surg.* 1991; 78:651–655).

Once at the site of infection, PMNs perform phagocytic and degradative functions to combat the infectious agent. As part of the response to the infectious agent, PMNs generate superoxide anions, reactive oxygen species (ROS) to kill infested material and adhere to epithelial cells of mucosal surfaces or vascular endothelial cells of the blood vessels. As a consequence, the host can experience undesirable side effects during the elimination of the infectious agent such as, pain, swelling about the site, and nausea.

SUMMARY OF THE INVENTION

The present invention relates to novel presqualene diphosphate (PSDP) analogs and their use.

In one embodiment, the present invention is directed to a PSDP analog having an active region of natural PSDP and a metabolic transformation region resistant to in vivo metabolism. For example, the analog can inhibit leukocyte activation, leukocyte generation of active oxygen species, adhesion between a leukocyte cell and an epithelial cell or an endothelial cell or leukocyte generation of reactive oxygen species (ROS).

In another embodiment, the present invention is directed to a method for treating or preventing inflammation and/or an inflammatory response in the subject. The method includes administering to a subject an anti-inflammatory amount of a PSDP analog having an active region of natural PSDP and a metabolic transformation region resistant to in vivo metabolism.

In yet another embodiment, the present invention is directed to a compound represented by one of the formulae (Formulae I–IV):

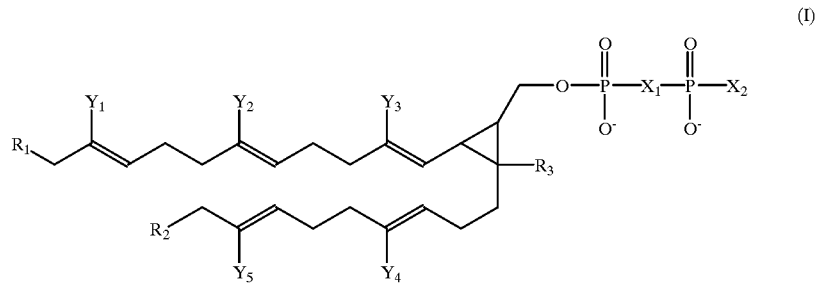

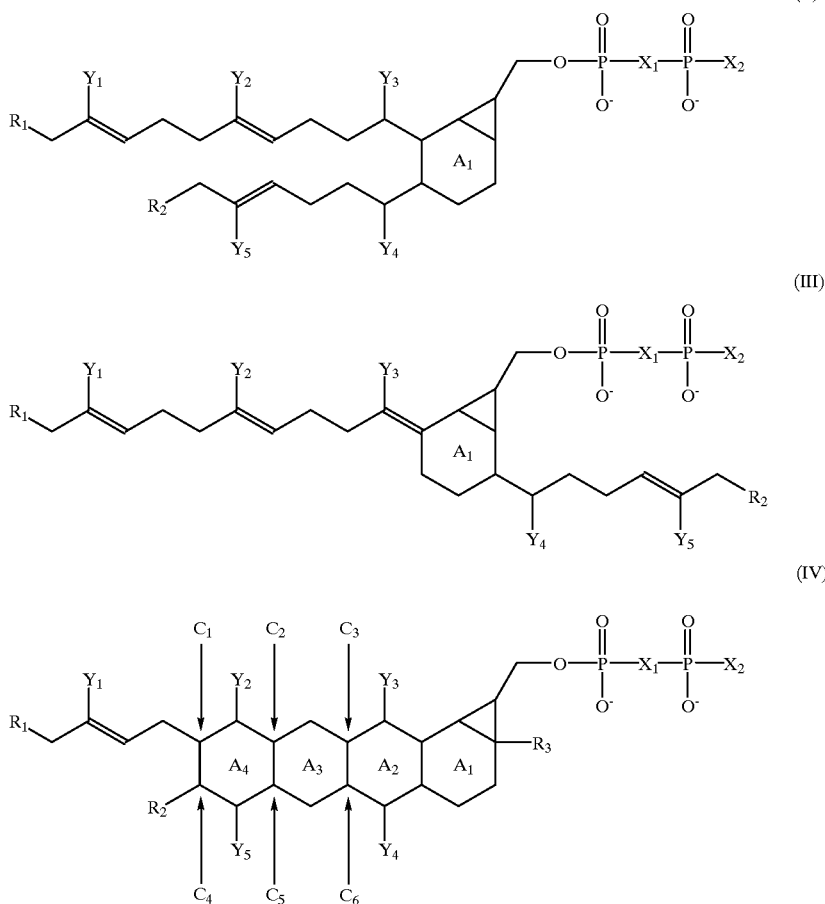

$R_1$, $R_2$ and $R_3$ are each independently, selected from the group consisting of hydrogen, F, Cl, Br, I, $CH_3$ and substituted or unsubstituted, linear or branched alkyl, alkoxy, aryl, aralkyl or heteroaryl groups. $Y_1$, $Y_2$, $Y_3$, $Y_4$, and $Y_5$ are each independently selected from hydrogen atoms or lower alkyl groups. $X_1$ is an oxygen atom, a sulfur atom, an N=N group, a methylene or, $NR_5$, wherein $R_5$ is a hydrogen atom or a substituted or unsubstituted, linear or branched alkyl, aryl, aralkyl or heteroaryl group. $X_2$ is an OH group, SH, $CH_3$, or $NR_6R_7$, wherein $R_6$ and $R_7$ are each independently, a hydrogen atom or a substituted or unsubstituted, linear or branched alkyl, aryl, aralkyl or heteroaryl group. $A_1$, $A_2$, $A_3$, and $A_4$ are each independently, a substituted or unsubstituted aromatic or nonaromatic carbocyclic or heterocyclic group. Preferably, carbon—carbon bonds are not formed between one or more of $C_1$ and $C_4$, $C_2$ and $C_5$, and $C_3$ and $C_6$ carbon atoms. Salts of Formulae I–IV are also included in the present invention.

In yet another embodiment, the present invention is directed to a pharmaceutical composition comprising an effective amount of a compound represented by one or more of the formulae (Formulae I–IV):

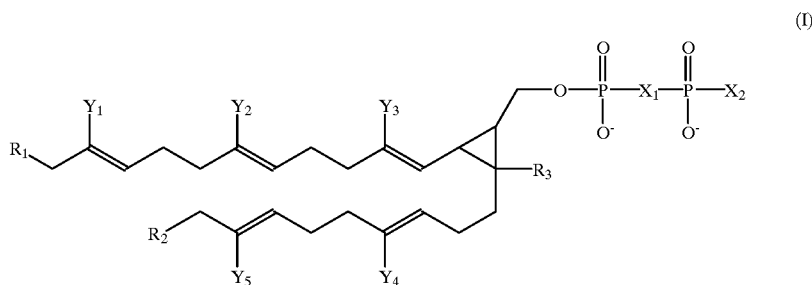

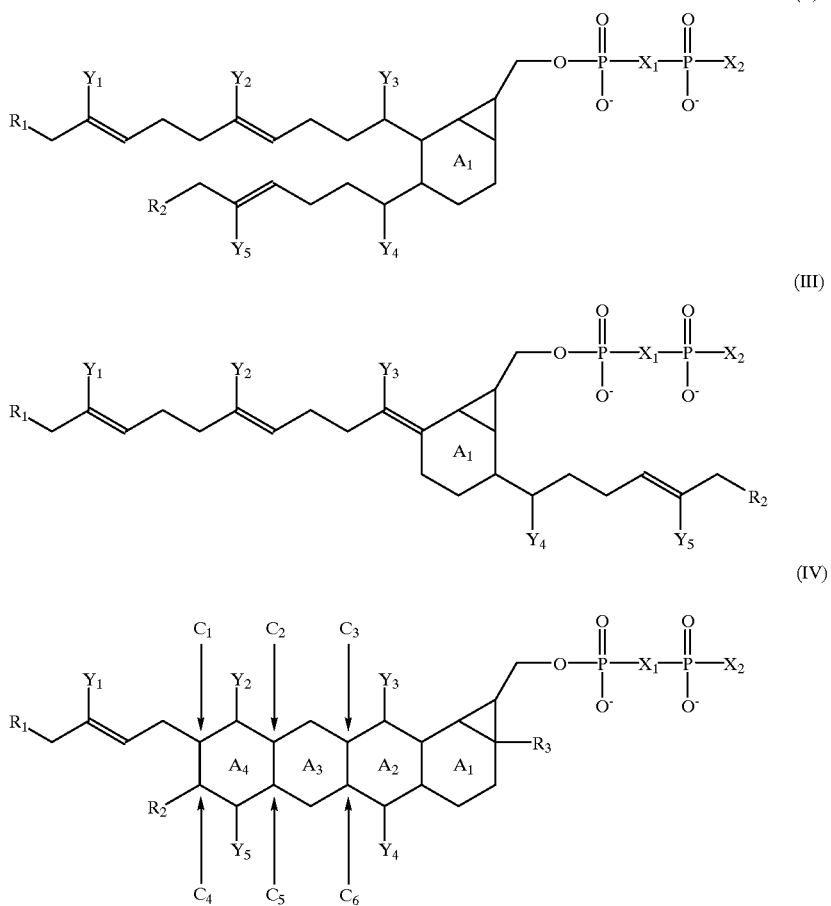

R₁, R₂ and R₃ are each independently, selected from the group consisting of hydrogen, F, Cl, Br, I, CH₃ and substituted or unsubstituted, linear or branched alkyl, alkoxy, aryl, aralkyl or heteroaryl groups. Y₁, Y₂, Y₃, Y₄, and Y₅ are each independently selected from hydrogen atoms or lower alkyl groups. X₁ is an oxygen atom, a sulfur atom, an N=N group, a methylene or, NR₅, wherein R₅ is a hydrogen atom or a substituted or unsubstituted, linear or branched alkyl, aryl, aralkyl or heteroaryl group. X₂ is an OH group, SH, CH₃, or NR₆R₇, wherein R₆ and R₇ are each independently, a hydrogen atom or a substituted or unsubstituted, linear or branched alkyl, aryl, aralkyl or heteroaryl group. A₁, A₂, A₃, and A₄ are each independently, a substituted or unsubstituted aromatic or nonaromatic carbocyclic or heterocyclic group. Preferably, carbon—carbon bonds are not formed between one or more of C₁ and C₄, C₂ and C₅, and C₃ and C₆ carbon atoms. The present invention also includes pharmaceutically acceptable salts of Formulae I–IV.

In still another embodiment, the invention is directed to a method for treating or preventing inflammation and/or an inflammatory response in the subject, comprising: administering to a subject an anti-inflammatory amount of more or more compounds having the formulae (Formulae I–IV):

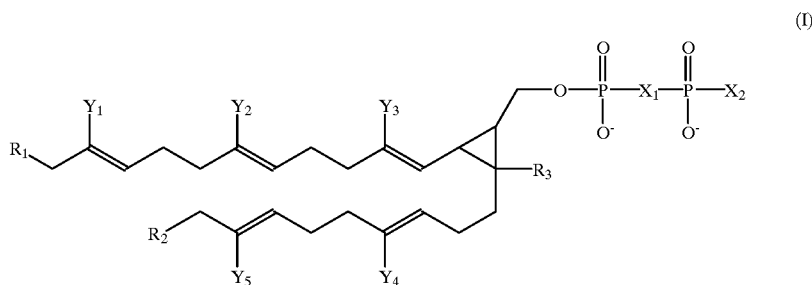

-continued

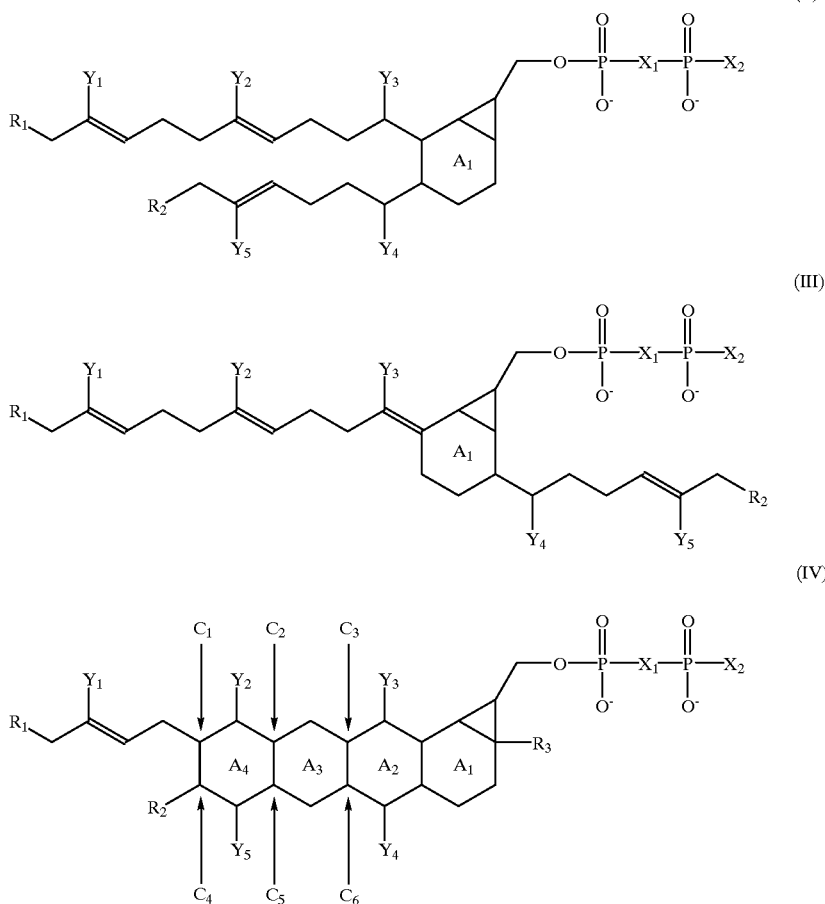

$R_1$, $R_2$ and $R_3$ are each independently, selected from the group consisting of hydrogen, F, Cl, Br, I, $CH_3$ and substituted or unsubstituted, linear or branched alkyl, alkoxy, aryl, aralkyl or heteroaryl groups. $Y_1$, $Y_2$, $Y_3$, $Y_4$, and $Y_5$ are each independently selected from hydrogen atoms or lower alkyl groups. $X_1$ is an oxygen atom, a sulfur atom, an N=N group, a methylene or, $NR_5$, wherein $R_5$ is a hydrogen atom or a substituted or unsubstituted, linear or branched alkyl, aryl, aralkyl or heteroaryl group. $X_2$ is an OH group, SH, $CH_3$, or $NR_6R_7$, wherein $R_6$ and $R_7$ are each independently, a hydrogen atom or a substituted or unsubstituted, linear or branched alkyl, aryl, aralkyl or heteroaryl group. $A_1$, $A_2$, $A_3$, and $A_4$ are each independently, a substituted or unsubstituted aromatic or nonaromatic carbocyclic or heterocyclic group. Preferably, carbon—carbon bonds are not formed between one or more of $C_1$ and $C_4$, $C_2$ and $C_5$, and $C_3$ and $C_6$ carbon atoms. The present invention also includes pharmaceutically acceptable salts of Formulae I–IV.

In still another embodiment, the present invention is directed to a method of screening for a compound which modulates phospholipase D (PLD) activity. The method includes combining the compound with phospholipase D (PLD), thereby forming a mixture and treating the mixture with phosphatidylcholine, such that a cleavage reaction between phosphatidylcholine and PLD can occur, resulting in generation of phosphatidic acid and choline. The amount of choline produced is evaluated such that a compound which modulates PLD activity is determined. In a preferred embodiment, the compound increases cleavage of phosphatidylcholine by PLD.

In still yet another embodiment, the present invention is directed to a method of screening for a compound which modulates intracellular signaling. The method includes combining a compound with phospholipase D (PLD), thereby forming a mixture and treating the mixture with phosphatidylcholine, such that a cleavage reaction between phosphatidylcholine and PLD occurs, resulting in generation of phosphatidic acid and choline. The amount of choline produced is evaluated, such that a compound which modulates intracellular signaling is determined.

In another embodiment, the invention is directed to a method of screening for a compound which associates with protein phosphate-sensing domains. The method includes contacting a Gst-Grb2 fusion protein complexed to a support with a labeled lipid compound with and evaluating the amount of labeled compound associated with the protein. The method can further include treating the labeled lipid compound associated with a competing compound and evaluating the amount of labeled compound removed from the Gst-Grb2 fusion protein.

In still another embodiment, the invention is directed to a method of screening for a compound which modulates the production of inositol triphosphate. The method includes treating polymorphoneutrophils with a stimulation agent, causing activation of cell, thereby producing inositol phosphate and treating the activated cells with a modulating compound. The effect of the modulating compound is measured on production of the inositol phosphate. A preferred stimulation agent is fMLP. A preferred modulating compound is PSDP, e.g., an inhibititory compound.

In yet another embodiment, the invention is directed to a method of screening for a compound which modulates neutrophil activation. The method includes treating neutrophils with a stimulation agent, causing activation of the neutrophils, thereby producing inositol phosphate and treating the activated neutrophils with a modulating compound. The effect of the modulating compound is measured on production of the inositol phosphate. A preferred stimulation agent is fMLP. A preferred modulating compound is PSDP, e.g., an inhibititory compound.

BRIEF DESCRIPTION OF THE DRAWINGS

FIG. 1g shows the ratio of mass determination by phosphorus quantitation compared to scanning densitometry.

FIG. 2e shows the physical chemical properties of compounds V–VIII.

DETAILED DESCRIPTION OF THE INVENTION

Figure 1A:
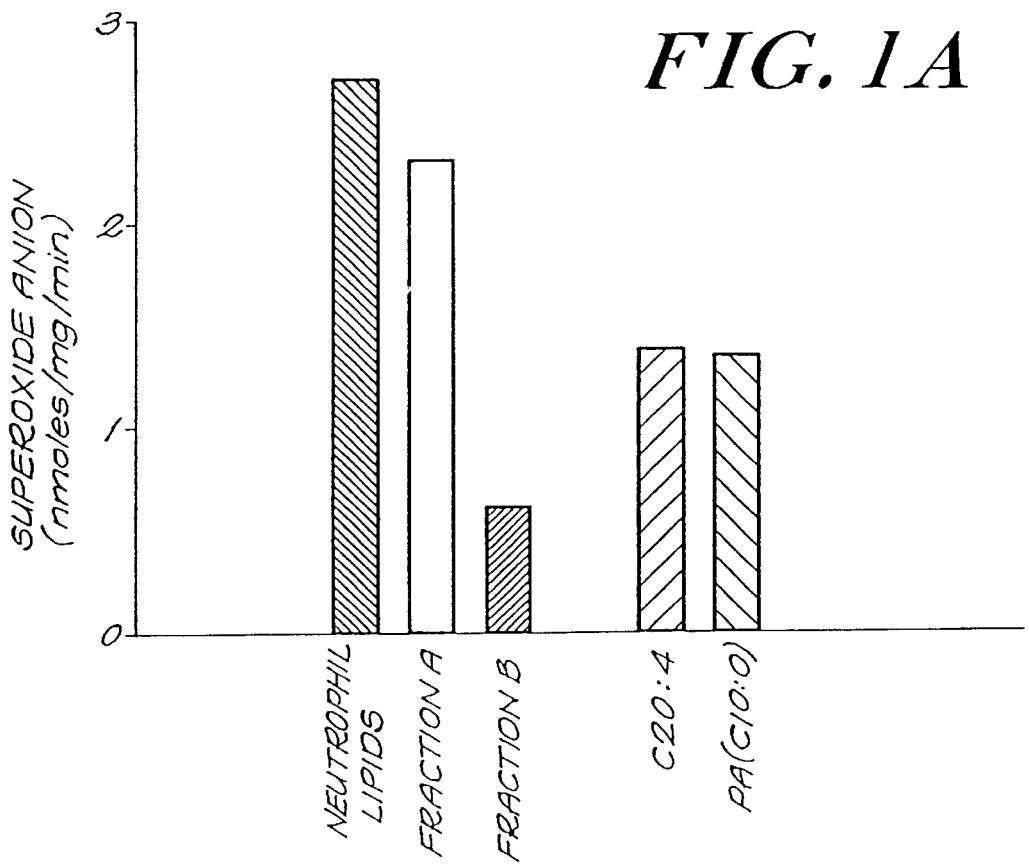
FIG. 1a depicts superoxide anion generation in the presence of neutrophil lipid extracts.
Figure 1B:
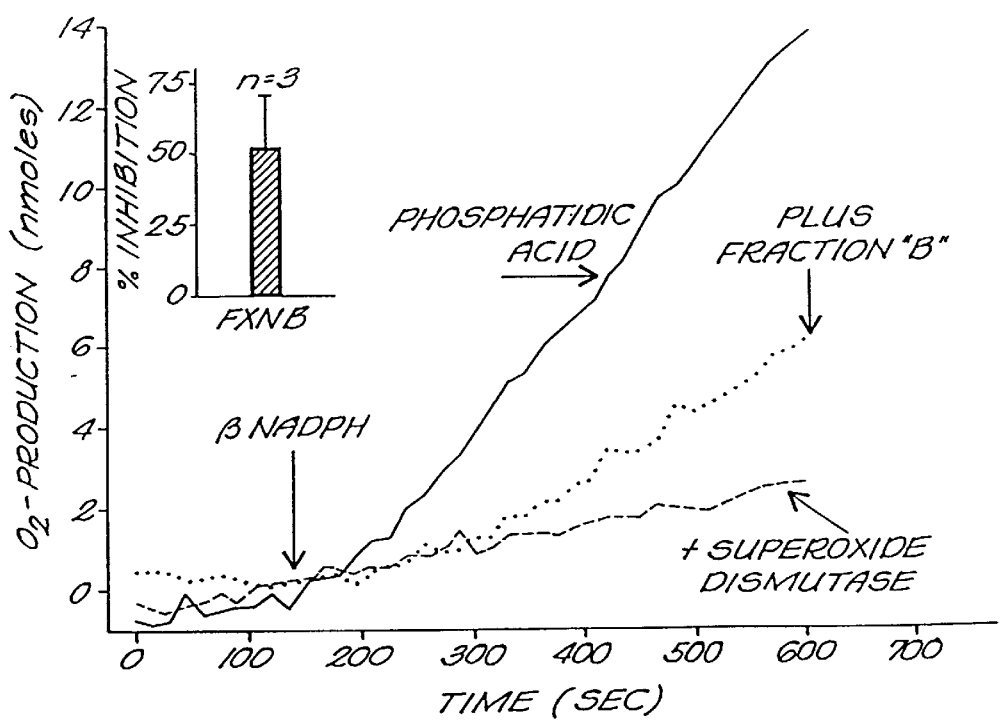
FIG. 1b is a representative time course for neutrophil Fraction B's inhibition of phosphatitic acid-triggered $O_2$-production.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

As used herein, the following phrases and terms are defined as follows:

The term "precursor" is intended to refer to chemical intermediates that can be converted in vivo, ex vivo and/or in vitro to form the PSDP analogs of the invention. The term "precursor" also contemplates prodrugs which are converted in vivo to the analogs of the invention (see, e.g., R. B. Silverman, 1992, "The Organic Chemistry of Drug Design and Drug Action", Academic Press, Chp. 8). Examples of such prodrugs include, but are not limited to esters of hydroxyls and/or carboxyl groups and/or compounds which can be hydrolyzed or otherwise converted in vivo or, ex vivo and/or in vitro into the analogs of the present invention.

The term "epithelial cells" includes epithelial cells of mucosal surfaces and/or endothelial cells of vascular origin.

The term "active region" shall mean the region of a natural PSDP or PSDP analog, which is associated with in vivo cellular interactions, e.g. inflammation. The active region may bind the "recognition site" of a cellular PSDP receptor or a macromolecule or complex of macromolecules, including an enzyme and its cofactor. Preferred PSDP analogs have an active region comprising the diphosphate moieties of natural PSDP.

The term "recognition site" or receptor is art-recognized and is intended to refer generally to a functional macromolecule or complex of macromolecules with which certain groups of cellular messengers, such as hormones, leukotrienes, PMNs and PSDP derivatives, must first interact before the biochemical and physiological responses to those messengers are initiated. As used in this application, a receptor may be isolated, on an intact or permeabilized cell, or in tissue, including an organ. A receptor may be from or in a living subject, or it may be cloned. A receptor may normally exist or it may be induced by a disease state, by an injury, or by artificial means. A compound of this invention may bind reversibly, irreversibly, competitively, noncompetitively, or uncompetitively with respect to the natural substrate of a recognition site.

The term "detectable label molecule" is meant to include fluorescent, phosphorescent, radiolabeled molecules, and other such labels as are conventional in the art used to trace, track, or identify the compound or receptor recognition site to which the detectable label molecule is bound. The label molecule may be detected by any of the several methods known in the art.

The term PSDP analog refers to analogs and derivatives of natural PSDP including structural or functional analogs which have the same or greater activity in vivo or in vitro as PSDP. Suitable examples of PSDP analogs include Formulae I–IV, supra.

The term "labeled PSDP analog" is further understood to encompass compounds which are labeled with radioactive isotopes, such as but not limited to tritium ($^3H$), deuterium ($^2H$), carbon ($^{14}C$), ($^{31}P$) or otherwise labeled (e.g. fluorescently). The compounds of this invention may be labeled or derivatized, for example, for kinetic binding experiments, for further elucidating metabolic pathways and enzymatic mechanisms, or for characterization by methods known in the art of analytical chemistry.

The term "inhibits" means the blocking or reduction of activity of a leukocyte, leukocyte generation of active oxygen species, or adhesion between a leukocyte cell and endothelial cell or an epithelial cell. The blockage or reduction can occur by covalent bonding, by irreversible binding, by reversible binding, e.g. which can have the practical effect of irreversible binding, or by any other means which prevents the leukocyte from operating in its usual manner.

The term "tissue" is intended to include intact cells, blood, blood preparations such as plasma and serum, bones, joints, muscles, smooth muscles, and organs, both in vivo and in vitro.

The term "halogen" is meant to include fluorine, chlorine, bromine and iodine, or fluoro, chloro, bromo, and iodo.

The term "pharmaceutically acceptable salt" is intended to include art-recognized pharmaceutically acceptable salts. These non-toxic salts are usually hydrolyzed under physiological conditions, and include organic and inorganic bases. Examples of suitable salts include sodium, potassium, calcium, ammonium, copper, and aluminum as well as primary, secondary, and tertiary amines, basic ion exchange resins, purines, piperazine, and the like. The term is further intended to include esters of lower hydrocarbon groups, such as methyl, ethyl, and propyl.

The term "pharmaceutical composition" comprises one or more PSDP analogs as active ingredient(s), or a pharmaceutically acceptable salt(s) thereof, and may also contain a pharmaceutically acceptable carrier and optionally other therapeutic ingredients. The compositions include compositions suitable for oral, rectal, ophthalmic, pulmonary, nasal, dermal, topical, parenteral (including subcutaneous, intramuscular and intravenous) or inhalation administration. The most suitable route in any particular case will depend on the nature and severity of the conditions being treated and the nature of the active ingredient(s). The compositions may be presented in unit dosage form and prepared by any of the methods well-known in the art of pharmacy. Dosage regimes may be adjusted for the purpose to improving the therapeutic response. For example, several divided dosages may be administered daily or the dose may be proportionally reduced over time. A person skilled in the art normally may determine the effective dosage amount and the appropriate regime. A PSDP analog pharmaceutic composition can also refer to a combination comprising PSDPs, PSDP analogs, and/or PSDP metabolites, including metabolites of PSDP analogs. A nonlimiting example of a combination is a mixture comprising a PSDP analog x which inhibits one enzyme which metabolizes PSDPs and which optionally has specific activity with a PSDP receptor recognition site, and a second PSDP analog y which has specific activity with a PSDP receptor recognition site and which optionally inhibits or resists PSDP metabolism. This combination results in a longer tissue half-life for at least y since x inhibits one of the enzymes which metabolize PSDPs. Thus, the PSDP action mediated or antagonized by y is enhanced.

The term "subject" is intended to include living organisms susceptible to conditions or diseases caused or contributed to by inflammation, inflammatory responses, vasoconstriction, myeloid suppression and/or undesired cell proliferation. Examples of subjects include warm blooded aminals, more preferably mammals such as humans, dogs, cats, cows, goats, and mice. The term subject is further intended to include transgenic species.

The term "ameliorate" is intended to include treatment for, prevention of, limiting of and/or inhibition of undesired leukocyte activation, leukocyte generation of oxygen active species, leukocyte generation of ROS and/or adhesion between a leukocyte cell and a epithelial cell or endothelial cells.

Active compounds are administered at a therapeutically effective dosage sufficient to inhibit leukocyte mediated responses, such as, leukocyte activation, leukocyte generation of oxygen species, leukocyte generation of ROS and/or adhesion between a leukocyte cell and an epithelial cell or endothelial cells in a subject. A "therapeutically effective dosage" preferably reduces the degree of leukocyte mediated responses in the subject by at least about 20%, more preferably by at least about 40%, even more preferably by at least about 60%, and still more preferably by at least about 80% relative to untreated subjects. The ability of a compound to inhibit or ameliorate leukocyte mediated responses can be evaluated in an animal model system that may be predictive of efficacy in treating said responses.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxy alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl arnino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (benzyl)).

The term "aryl" as used herein includes 5- and 6-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. Aryl groups can also be fused or bridged with alicyclic or heterocyclic rings which are not aromatic so as to form a polycycle (e.g., tetralin).

Unless the number of carbons is otherwise specified, "lower alkyl" as used herein means an alkyl group, as defined above, but having from one to ten carbons, more preferably from one to six carbon atoms in its backbone structure. Preferred alkyl groups are lower alkyls.

The terms "heterocyclyl" or "heterocyclic group" refer to 3- to 10-membered ring structures, more preferably 4- to 7-membered rings, which ring structures include one to four heteroatoms. Heterocyclyl groups include pyrrolidine, oxolane, thiolane, oxazole, piperidine, piperazine, morpholine, lactones, lactams such as azetidinones and pyrrolidinones, lactones, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. A heteroalkyl moiety is an alkyl substituted with a heteroaromatic group.

The terms "polycyclyl" or "polycyclic group" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, aralkyl, or an aromatic or heteroaromatic moiety.

The term "heteroatom" as used herein means an atom of any element other than carbon or hydrogen. Preferred heteroatoms are nitrogen, oxygen, sulfur and phosphorus.

The term "substantially pure," as used herein, refers to a compound which is substantially free of impurities, including (but not limited to) starting materials, side products, and the like. A compound is "substantially pure" if it comprises at least about 80%, more preferably 90%, still more preferably at least about 95% of the composition. If a single isomer of a compound is desired (e.g., a single diastereomer, enantiomer, or regioisomer), the compound is preferably substantially free of any undesired isomers (e.g., the unwanted enantiomer, diastereomers, or regioisomers), i.e., the desired isomer comprises at least about 80%, more preferably 90%, still more preferably at least about 95% of the weight of the isomers present in the composition.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis.

I. PSDP Analogs

The instant invention is based on the surprising finding that PSDP ameliorates potentionally undesirable leukocyte mediated responses during neutrophil activation, such as inhibition of the superoxide generating system. Applicants have discovered that PSDP inhibits key neutrophil responses, which are important in leukocyte-mediated tissue injury as observed in reperfusion injury or overt acute inflammatory resonses. Based upon these findings, a series of PSDP analogs that resist rapid inactivation of PSDP have been designed in order to prevent or control the unwanted release of noxious agents from activated neutrophils. The PSDP analogs of the present invention include, compounds which can be represented by Formulae I–IV:

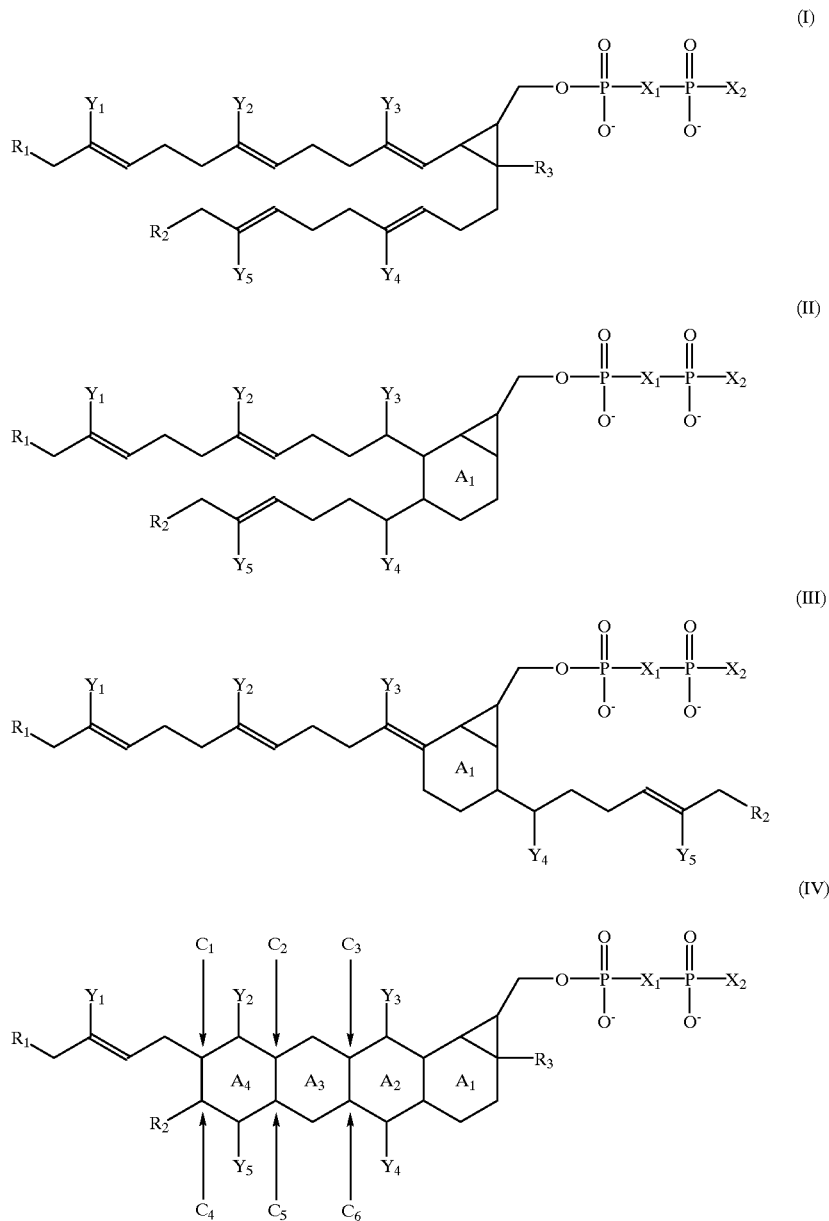

wherein $R_1$, $R_2$ and $R_3$ are each independently, selected from the group consisting of hydrogen, F, Cl, Br, I, $CH_3$ and substituted or unsubstituted, linear or branched alkyl, alkoxy, aryl, aralkyl or heteroaryl groups;

wherein $Y_1$, $Y_2$, $Y_3$, $Y_4$, and $Y_5$ are each independently selected from hydrogen atoms or lower alkyl groups;

wherein $X_1$ is an oxygen atom, a sulfur atom, an N=N group, a methylene or, $NR_5$, wherein $R_5$ is a hydrogen atom or a substituted or unsubstituted, linear or branched alkyl, aryl, aralkyl or heteroaryl group;

wherein $X_2$ is an OH group, SH, $CH_3$, or $NR_6R_7$, wherein $R_6$ and $R_7$ are each independently, a hydrogen atom or a substituted or unsubstituted, linear or branched alkyl, aryl, aralkyl or heteroaryl group; and wherein $A_1$, $A_2$, $A_3$, and $A_4$ are each independently, a substituted or unsubstituted aromatic or nonaromatic carbocyclic or heterocyclic group or a salt thereof.

In preferred embodiments of the compound of Formulae I and II, $Y_{1-5}$ are F or $CH_3$, X is N=N or methylene and $X_2$ is OH.

It has now been unexpectedly found that the compounds of the invention inhibit leukocyte mediated responses. For example, as described in FIG. 1, infra, certain compounds of the invention have activity against superoxide anion. Moreover, the compounds of the invention can have a variety of closely spaced functionalities and may serve as interesting molecular scaffolds. The leukocyte-mediated inflammation or inflammatory responses cause or contribute to a wide variety of diseases and conditions including various forms of asthma and arthritis. Included within the present invention are inflammatory responses to physical injury, such as physical trauma, radiation exposure, and otherwise. The compounds of the invention can be used to treat inflammatory related disorders, such as rheumatoid arthritis, asthma, psoriasis, related leukocyte dependent reperfusion injury and adult respiratory distress syndrome (ARDS).

II. Preparation of PSDP Analogs

Derivatives of farnesyl diphosphate (1) can be incorporated into analogs of presqualene diphosphate (2) (PSDP) by enzymatic synthesis using squalene synthetase in the absence of reducing conditions (as in Jarstfer, M. B. et al., J. Am. Chem. Soc. 1996, 118, 13089).

or unsubstituted linear or branched alkyl, alkoxy, aryl, aralkyl or heteroaryl groups, as described previously. Each Y group can be independently selected from hydrogen or substituted or unsubstituted alkyl groups, preferably methyl, ethyl or propyl groups. $R_1$, $R_2$, $R_3$ and the Y groups help stabilize the PSDP analog to prevent inactivation by $P_{450}$ oxidation and slow first pass metabolism in the liver, kidneys and lungs.

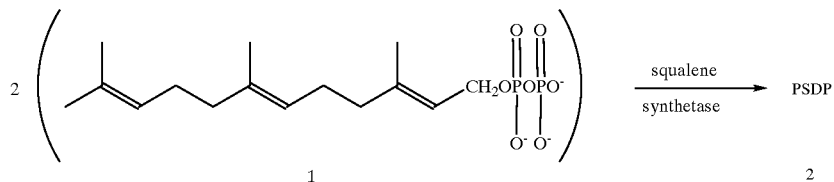

Only minor variations in the farnesyl diphosphate structure are recognized by squalene synthetase (Ortiz de Montellano, P. R. et al., Biochemistry 1977, 16, 2680), therefore, synthesis of complex analogs of presqualene diphosphate require that structural similarity is retained. Analogs of PSDP can be prepared by chemical syntheses as described below and can be prepared by standard techniques including Wittig-type coupling, Grignard synthesis, carbene addition, selective hydrogenation, epoxidation and asymmetric reductions. For example, presqualene derivatives have been prepared by Jarstfer et al., J. Am. Chem. Soc. 1996, 118, 13089; Cohen L. H. et al., Biochem. Pharmacol. 1995, 49(6), 839; Poulter C. D., Rilling H. C. in Biosynthesis of Isoprenoid Compounds 1981, Vol. 1, Chap. 8, 413; Corey E. J., Volante R. P., J. Am. Chem. Soc. 1975, 98, 1291; Coates R. M., Robinson W. H., J. Am. Chem. Soc. 1971, 93, 1785; Good R. S., Eckstein F., J. Am. Chem. Soc. 1971, 93, 6252; Kornforth R, Popjak G., Methods Enzymol. 1969, 15, 382), the teachings of which are incorporated herein by reference.

In one exemplary synthesis, PSDP analogs of the invention can be prepared in three major fragments (A, B and C). These fragments can then be combined, under appropriate conditions, to form (3). $R_1$, $R_2$, $R_3$, $Y_1$, $Y_2$, $Y_3$, $Y_4$, $Y_5$, $X_1$ and $X_2$ are as described above.

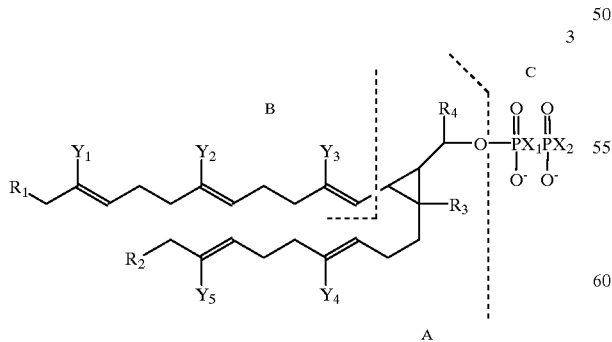

Polyisoprenyl alcohol precursors (4a) and (4b) can be prepared with substituents $R_1$ or $R_2$, independently selected from halogen (e.g., F, Cl), hydrogen, methyl and substituted

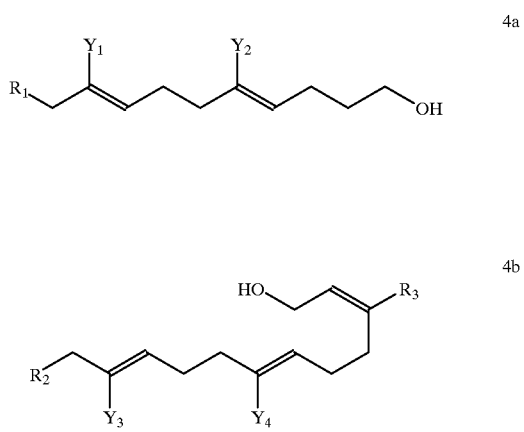

The method of Coates and Robinson (J. Am. Chem. Soc. 1971, 93, 1785) can be modified to couple polyisoprenyl alcohol (4b) (fragment B) to cyclopropylcarbinyl ring (fragment A). Polyisoprenyl alcohol (4b) (fragment B) can be transformed into diazoacetate derivative (5) by treatment with glyoxalyl chloride tosylhydrazone and triethylamine in methylene chloride (House H. O., Blankley C. J., J. Org. Chem. 1963, 33, 53).

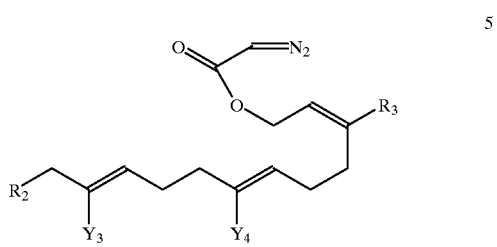

Transformation of (5) by copper-catalyzed decomposition with cupric acetylacetonate in refluxing toluene can result in formation of cyclopropyl lactone (6) having a cis-formed lactone ring.

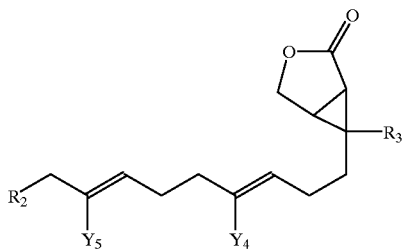

6

Cyclopropyl lactone (6) can be hydrolyzed to hydroxy acid (7) which can be further oxidized to cis-aldehyde acid (8) with chromium trioxide-dipyridine complex in methylene chloride.

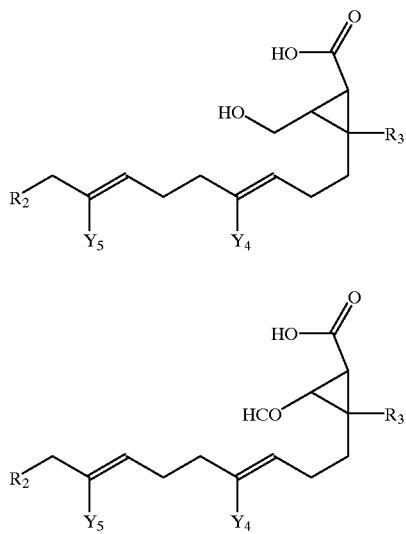

7

8

Aldehyde ester (8) can then be esterfied with diazomethane to yield ester (9).

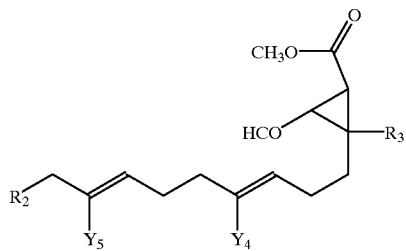

9

A second polyisoprenyl side chain (4a) can be converted to phosphorane derivative (13). For example, polyisoprenyl alcohol (4a) can be treated with tosyl

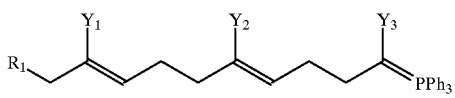

13 chloride, sodium iodide-acetone and triphenylphosphine in benzene, to generate primary phosphonium iodide (10).

Deprotonation of (10) with n-butyllithium in ether followed

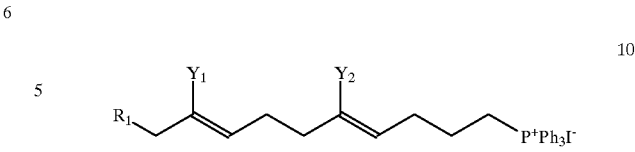

10 by alkylation with an excess of an alkyl halide, such as, for example methyl iodide, can yield monosubstituted ylide (11), thereby producing second phosphonium iodide (12).

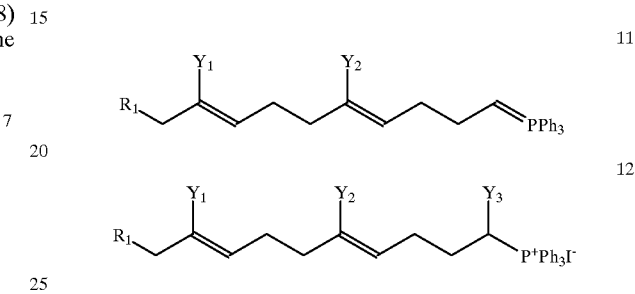

11

12

Addition of a second equivalent of n-butyllithium to (12) in tetrahydrofuran generates the disubstituted ylide (13).

A Wittig reaction between ester (9) and ylide (13) in tetrahydrofuran can produce an isomeric mixture of esters (14). Reduction of esters (14) with lithium aluminum hydride affords corresponding alcohols (15) which can be separated by chromatography.

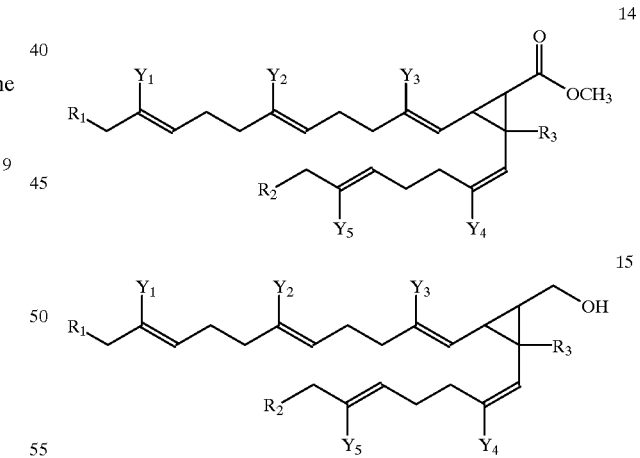

14

15

To generate diphosphorylated analog (16), one mmole of alcohol (15) can be added to trichloroacetonitrile (6 mmoles) followed by addition of di-triethylammonium phosphate (2.4 mmoles) dissolved in acetonitrile over 3–4 h at room temperature. Diphosphate (16) can be extracted with 0.1 N aqueous ammonia and ether and isolated by techniques known to those skilled in the art (as in Komforth R., Popjak G., Methods Enzymol. 1969, 15, 382).

16

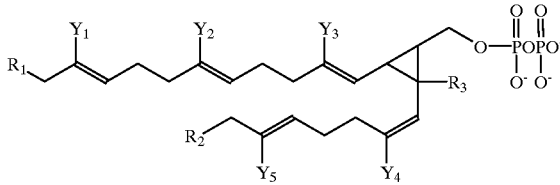

In another embodiment, modification of the synthesis of GTPγS (Goody R. S., Eckstein F., J. Am. Chem. Soc. 1971, 93, 6252) provides presqualene diphosphate analogs with sulfur in the $X_1$ and $X_2$ positions. For example, the lithium salt of S-2-carbamoylethyl thiophosphate (17) (R=2 carbamoylethyl) can be converted to a pyridinium salt via ion exchange column and then to a mono(tri-n-octylammonium) salt by addition of tri-n-octylamine in methanol. The solution is concentrated under reduced pressure to afford a residue which is suspended in dixoane and combined with diphenyl phosphorochloridate and tri-n-butylamine to yield (18).

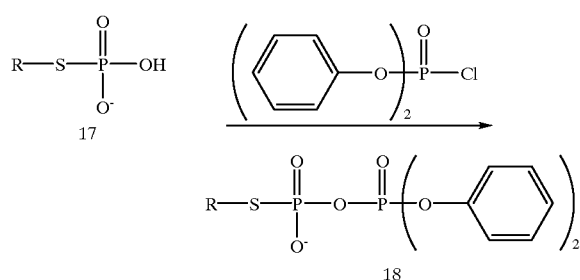

Conversion of the polyisoprenyl alcohol (15) to a monophosphorylated derivative can be accomplished by adding (15) in pyridine and ether drop-wise over 30 min to freshly distilled $POCl_3$/ether at −10° C. with stirring. Pyridine HCl is removed by filtration. Lithium hydroxide can then be added to the filtrate, followed by aqueous ammonia until a pH of 12 is reached. Inorganic trilithium phosphate salt can be removed from the solution by centrifugation and contaminates are removed by extraction with ethanol/water. The pH of the supernatant can be adjusted to 8 with HCl. Lyophilization of the remaining solution yields monophosphorylate derivative (19).

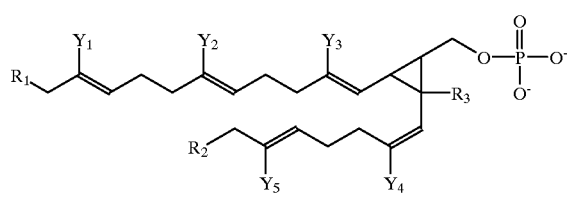

Compound (18) can be treated with ether and added to (19) in pyridine at room temperature to produce diphosphorylated analog (20). Similarly, reaction of (15) with (18) can produce monophosphorylated analog (21) with sulfur in the $X_1$ position. Additionally (21) can also be a substrate for a second phosphorylation by (18) to yield sulfur in both the $X_1$ and $X_2$ positions. Therefore, when R═H in compound (21), further reaction with (18) can yield (22).

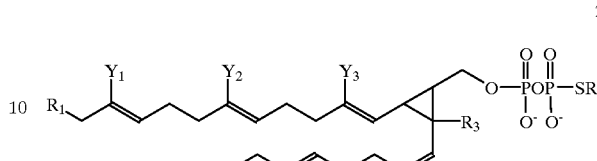

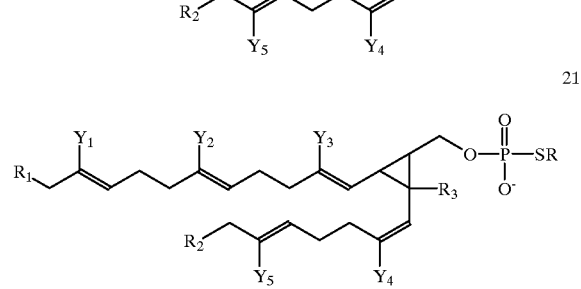

In yet another embodiment, the present invention provides analogs of PSDP, such as (23), which incorporate at least one ring system, $A_1$, into the molecule. These PSDP analogs can also be prepared from fragments A, B and C (shown in (23)), which can be coupled to form (23). As described above, $A_1$ can be a substituted or unsubstituted aromatic or non-aromatic carbocyclic or heterocyclic ring. The presence of $A_1$ can help stabilize the conformation of (23).

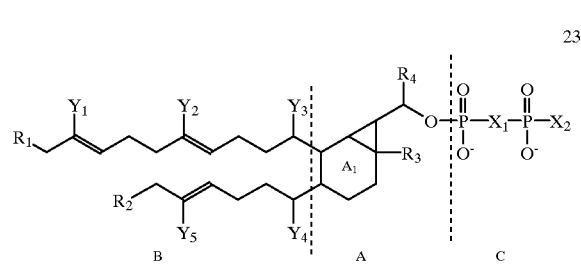

For example, fragment B can be coupled to fragment A, thereby forming a compound which can be phosphorylated as described above. In one embodiment, fragment B can be prepared by dehalogenating 1,4-dichlorocyclohexane (24) to conjugated diene (25). This dehalogenation provides a substrate suitable for addition of chlorocarbene to form cyclopropylcarbinyl ring (26). Compound (26) can then undergo syn addition epoxidation in the presence of performic acid to form (27). Hydrolysis of (27) can then form diol (28). Alternatively, exposure of cyclopropyl chloride (26)

24

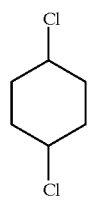

25

26

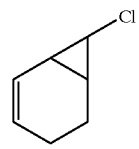

27

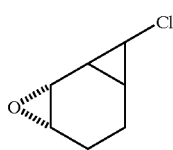

to osmium tetroxide can produce diol (28). Oxidation of the hydroxyl groups of (28), followed by Grignard addition of suitable alkyl groups and subsequent reduction of resultant alcohols provides (29). Conversion of the chloride to a hydroxyl group leads to (30) which can be derivatized as described above.

28

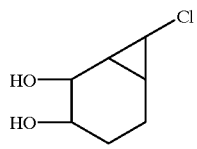

29

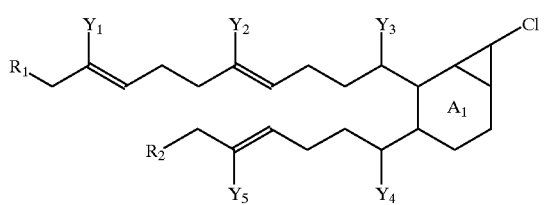

30

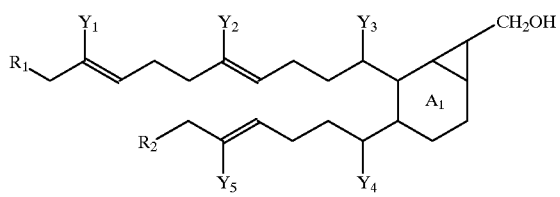

Each of the PSDP analogs and their intermediates can be isolated by chromatography (TLC, RP-HPLC) for homogeneity.

III. Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a compound of the present invention which is effective for producing some desired therapeutic effect by treating (i.e., inhibiting, preventing or ameliorating) a bacterial infection or a leukocyte mediated response in a subject, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject peptidomimetic agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds can contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1–19)

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal action, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as bronchoaveolar lavages for intended delivery systems to the lung and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar—agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum and release the active compound.

Formulations of the present invention which are suitable for vaginal administration also include pessaries, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the peptidomimetic in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 0.1 to about 40 mg per kg per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

IV. Examples

Receptor-ligand recognition initiates membrane remodeling events that generate bioactive lipids which serve as both inter- and extracellular mediators crucial to coordinate leukocyte responses (Serhan, C. N., Haeggström, J. Z. & Leslie, C. C. FASEB J. 10:1147–1158 (1996), the teachings of which are incorporated herein by reference.). While several classes of prophlogistic lipids have been described (Serhan, C. N., Haeggström, J. Z. & Leslie, C. C. FASEB J. 10:1147–1158 (1996)), the present invention is directed to novel intracellular lipid signals that down-regulate neutrophil responses. Neutrophil-derived extracts rich in phosphorylated, non-saponifiable lipids potently inhibit superoxide anion generation. Structural analysis of these bioactive fractions revealed four major phosphorylated lipids: (V) farnesyl diphosphate, (VI) presqualene diphosphate (PSDP), (VII) farnesyl monophosphate and (VIII) presqualene monophosphate (PSMP). Following receptor activation, compounds VI and VIII underwent rapid phosphate turnover. Compound VI but not VIII, in nM-$\mu$M amounts, inhibited neutrophil superoxide anion generation, homotypic adhesion and 1,4,5-inositol-triphosphate formation. These results indicate that PSDP, present in immune effector cells, is a potent receptor-activated mediator which regulates cellular responses of interest in inflammation and tissue injury.

Receptor-ligand interaction results in the elaboration of both positive and negative signals, the timing and balance of which determines cellular responses (Serhan, C. N., Haeggström, J. Z. & Leslie, C. C. FASEB J. 10:1147–1158 (1996)). This phenomenon is exemplified by formyl-methionyl-leucyl-phenylalanine (FMLP) binding to its receptor on neutrophils with subsequent generation of intracellular signals that stimulate (e.g., intracellular calcium influx) as well as inhibit (e.g. formation of cyclic AMP) neutrophil function (Weismann, G., Smolen, J. E. & Korchak, H. M. N. Engl. J. Med. 303, 27–34 (1980), the teachings of which are incorporated herein by reference). Although several classes of intracellular lipids are known to activate leukocytes during inflammation and reperfusion injury, relatively few counterregulatory lipid-derived mediators have been identified (Serhan, C. N., Haeggström, J. Z. & Leslie, C. C. FASEB J. 10:1147–1158 (1996)). To this end, the capacity of neutrophil extracts to regulate superoxide anion generation was screened with cell sonicates.

Neutrophil-derived lipid extracts triggered generation of substantial amounts of superoxide anions (2.71 nmoles $O_2$-/mg protein/min) (FIG. 1a). To identify regulatory signals, phospholipids with ester or amide bonds were hydrolyzed by saponification prior to extraction and CC4 silica chromatography (generally, as in Adair, W. L. & Keller, R. K. Methods Enzymol. 111, 201–215 (1985); Van Dessel, G. A. F., Lagrou, A. R. Hilderson, H. J. J. & Dierick, W. S. H. In: CRC *Handbook of Chromatography* (eds Mukherjee, K. D., Weber, N. & Sherma, J.) 321–337 (CRC Press, Boca Raton, 1993), the teachings of which are incorporated herein by reference). The initial chloroform:methanol (2:1, v/v) elutions (Fraction "A") contained a mixture of fatty acids and neutral lipids that gave similar rates of superoxide anion generation (2.31 nmoles/mg protein/min). $O_2$- production was comparable to that observed with arachidonic acid (C20:4 (75 µM), 1.38 nmoles/mg protein/min) and phosphatitic acid (C10:0 (100 µM), 1.34 nmoles/mg protein/min), known activators in this system, and consistent with reported values (FIG. 1a) (as in references: McPhail, L. C., Shirley, P. S., Clayton, C. C. & Snyderman, R. J. Clin Invest. 75, 1735–1739 (1985) and Agwu, D. E., McPhail, L. C., Sozzani, S., Bass, D. A. & McCall, C. E. J Clin. Invest. 88, 531–539 (1991), the teachings of which are incorporated herein by reference). In contrast, subsequent elutions with chloroform: methanol:water (10:10:3, v/v) (Fraction "B"), which contained non-saponifiable, phosphorylated lipids, stimulated much less superoxide anion generation (0.62 nmoles/mg protein/min). Furthermore, the lipids present in Fraction B potently inhibited $O_2$- production stimulated by either phosphatitic acid (52%, FIG. 1f) or arachidonic acid (56%, see FIG. 1b). These results indicate that materials present in Fraction B can counteract intracellular lipid signals relevant in early neutrophil activation.

Characterization of PSDP analogs and metabolites include standard techniques such as extraction, chromatography, and quantitative HPLC followed by trimethyl silyl derivatization, O-methoxime derivatization and gas chromatography/mass spectroscopy analysis. The experimental details of this embodiment are described above.

Neutrophil lipids were saponified (10% KOH in methanol, 37° C., 30 min), extracted (Van Dessel, G. A. F., Lagrou, A. R. Hilderson, H. J. J. & Dierick, W. S. H. In: CRC *Handbook of Chromatography* (eds Mukherjee, K. D., Weber, N. & Sherma, J.) 321–337 (CRC Press, Boca Raton, 1993)) and separated by CC4 silica (1 gm/$10^8$ PMN) column chromatography as in FIG. 1f. To determine $O_2$- production, post-nuclear supernatants from neutrophils after sonication (as in McPhail, L. C., Shirley, P. S., Clayton, C. C. & Snyderman, R. J. Clin Invest. 75, 1735–1739 (1985)), 75 µM arachiodonic acid(C20:4, NuCheck Prep) and Fraction B (0.1% ethanol) were added to cytochrome c (60 µM), sucrose (170 mM), EGTA (ethylene glycol-bis (β-aminoethyl ether)-N,N,N',N'-tetraacetic acid). (1 mM), FAD (flavin adenine dinucleotide) (10 µM), $NaN_3$ (2 mM) and either superoxide dismutase (30 µg/ml) or $H_2O$ at 0° (as in 20). After 2 min (37° C.) in a thermal-jacketed cuvette, β-NAPH (200 µM) was added to initiate reactions and absorbance (550 nm) was monitored at 15 second intervals. Representative results are depicted from n=6. The inset shows % inhibition of arachidonic acid-stimulated superoxide anion generation by Fraction B lipids. Values represent mean±Standard Error of the Mean.

Figure 1C:
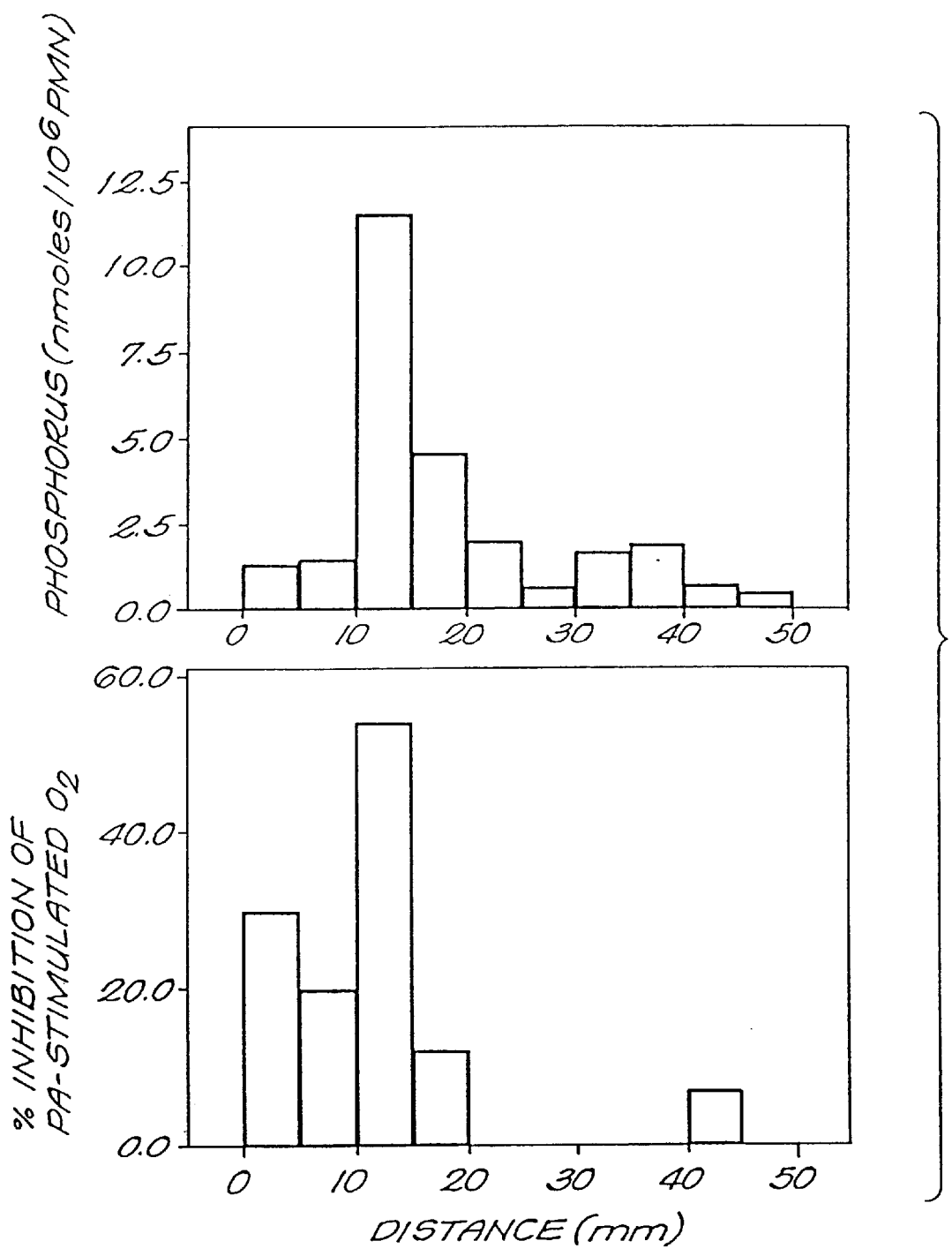
FIG. 1c shows Fraction B phosphorus content and bioactivity in sequential TLC segments.
Figure 1D:
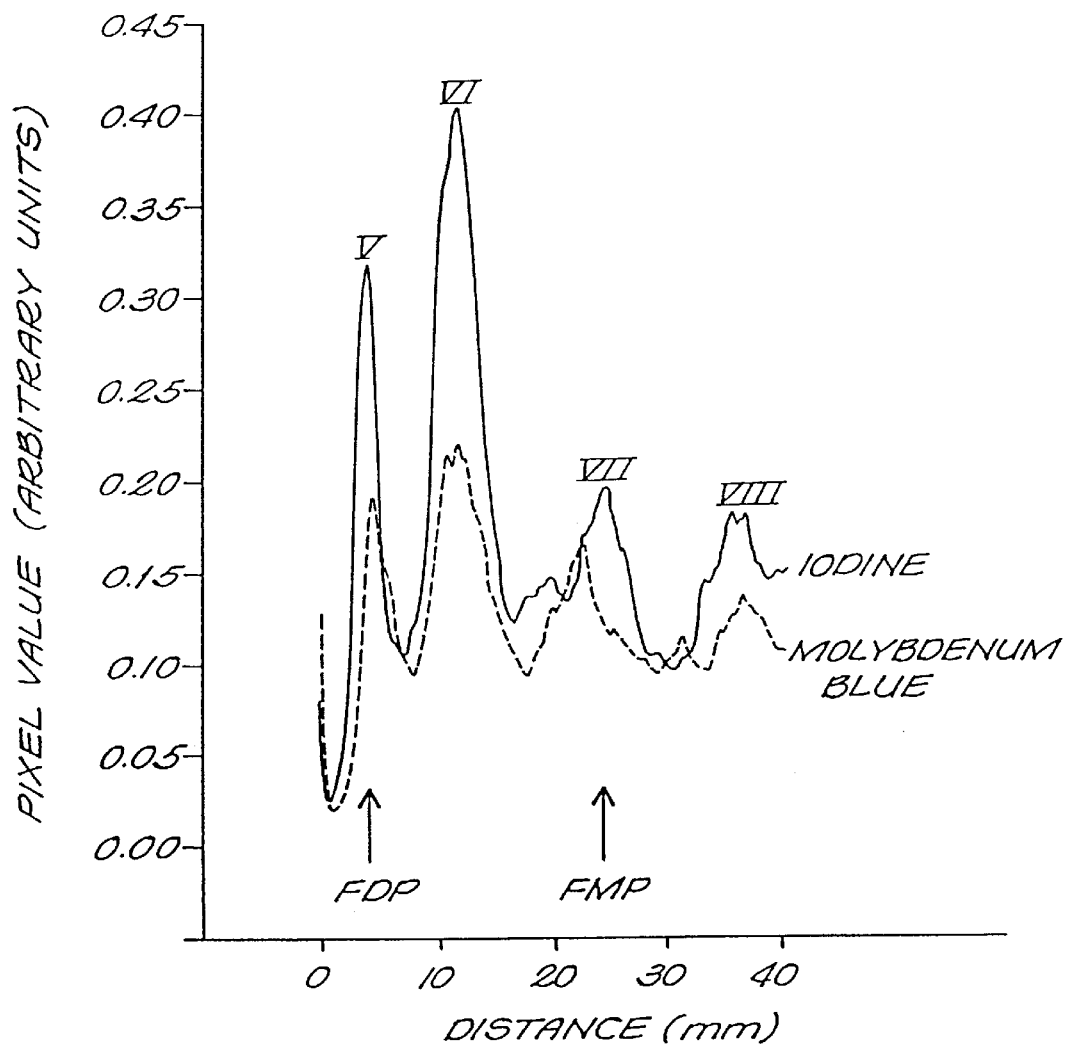
FIG. 1d is a representative densitometric analysis of Fraction B nonsaponifiable phosphorus containing lipids
Figure 2A:
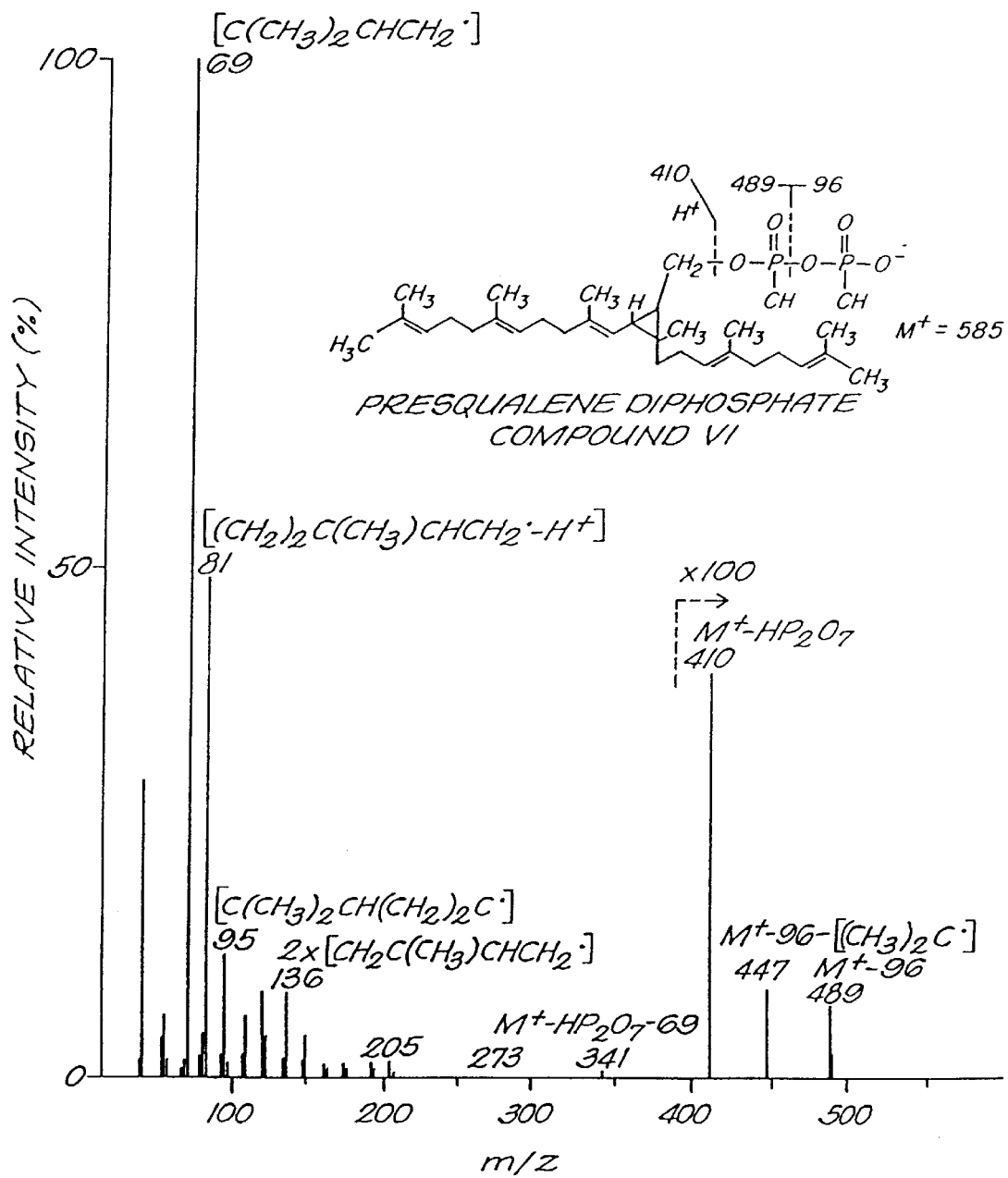
FIG. 2a is a mass spectrum of compound VI, consistent with presqualene diphosphate.
Figure 2B:
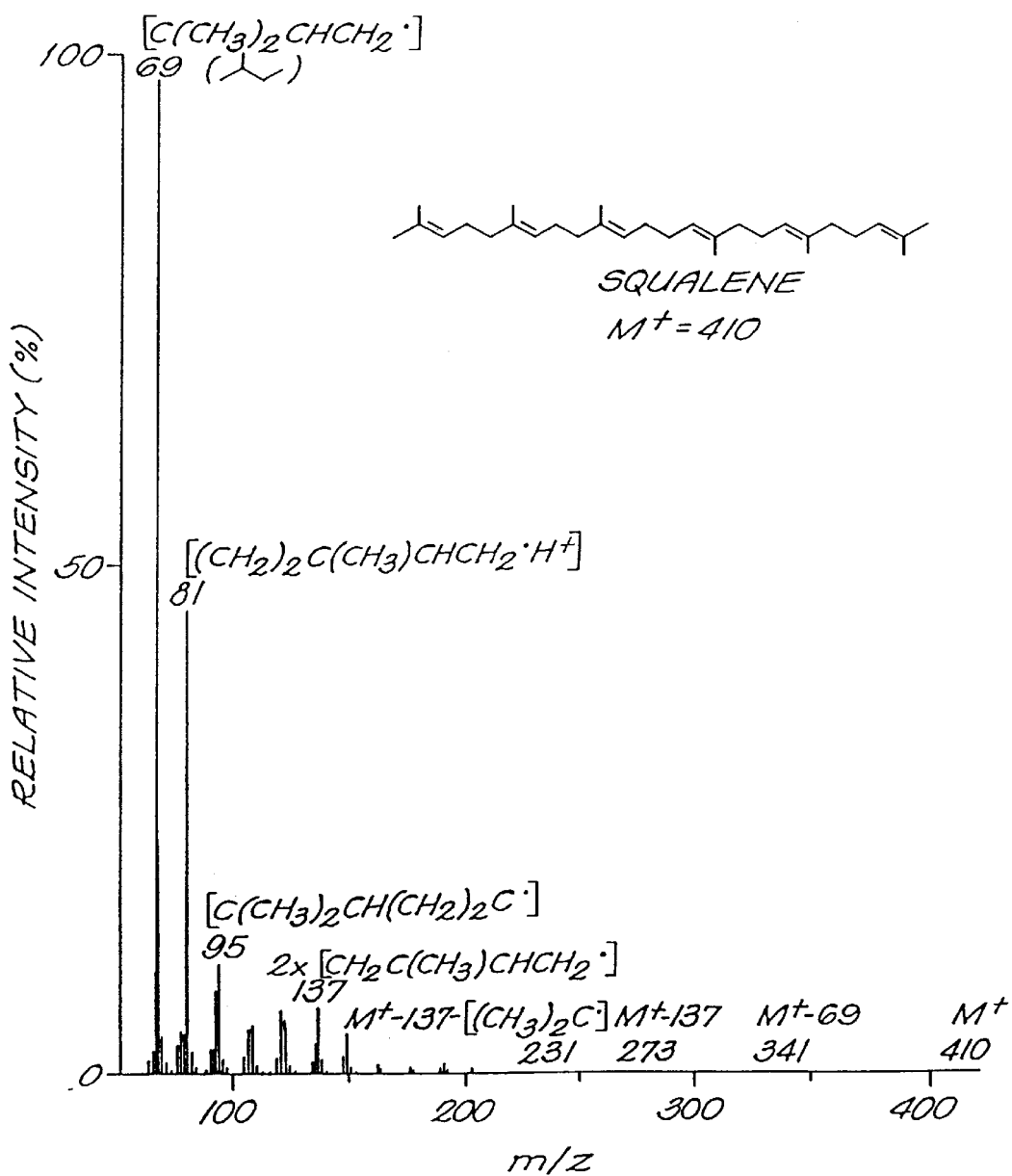
FIG. 2b is a limited ion chromatogram for m/z 136 (i.e., 2 internal isoprene units) after direct injection.

To identify the inhibitory compounds in Fraction B, extracts, isolated from stimulated neutrophils, were examined after thin layer chromatography (TLC). Lipids were eluted from sequential 5 mm fractions from origin to solvent front and assessed for phosphorus content and bioactivity. Regions 10–15 mm from the origin carried phosphorus (11.3 nmoles phosphorus/$10^6$ PMN) and resulted in a 52% inhibition of phosphatitic acid stimulated superoxide anion generation (FIG. 1c). To determine the Rf value of Fraction B's bioactive, non-saponifiable phosphorus-containing lipids, materials chromatographed in parallel were stained with iodine to identify double bonds and treated with molybdenum blue to visualize phosphorus. Four major compounds were observed (FIG. 1d). In preliminary experiments to elucidate the structures, material analyzed by gas chromatography/mass spectrometry (GC/MS), gave base peaks at (m/z 69) with a fragmentation pattern of repeating $C_5H_8$ (m/z 68) units, characteristic of isoprenoids (FIG. 2d) (see, for example, Farnsworth, C. C., Gelb, M. H. & Glomset, J. A. *Science* 247, 320–322 (1990), the teachings of which are incorporated herein by reference).

Figure 2C:
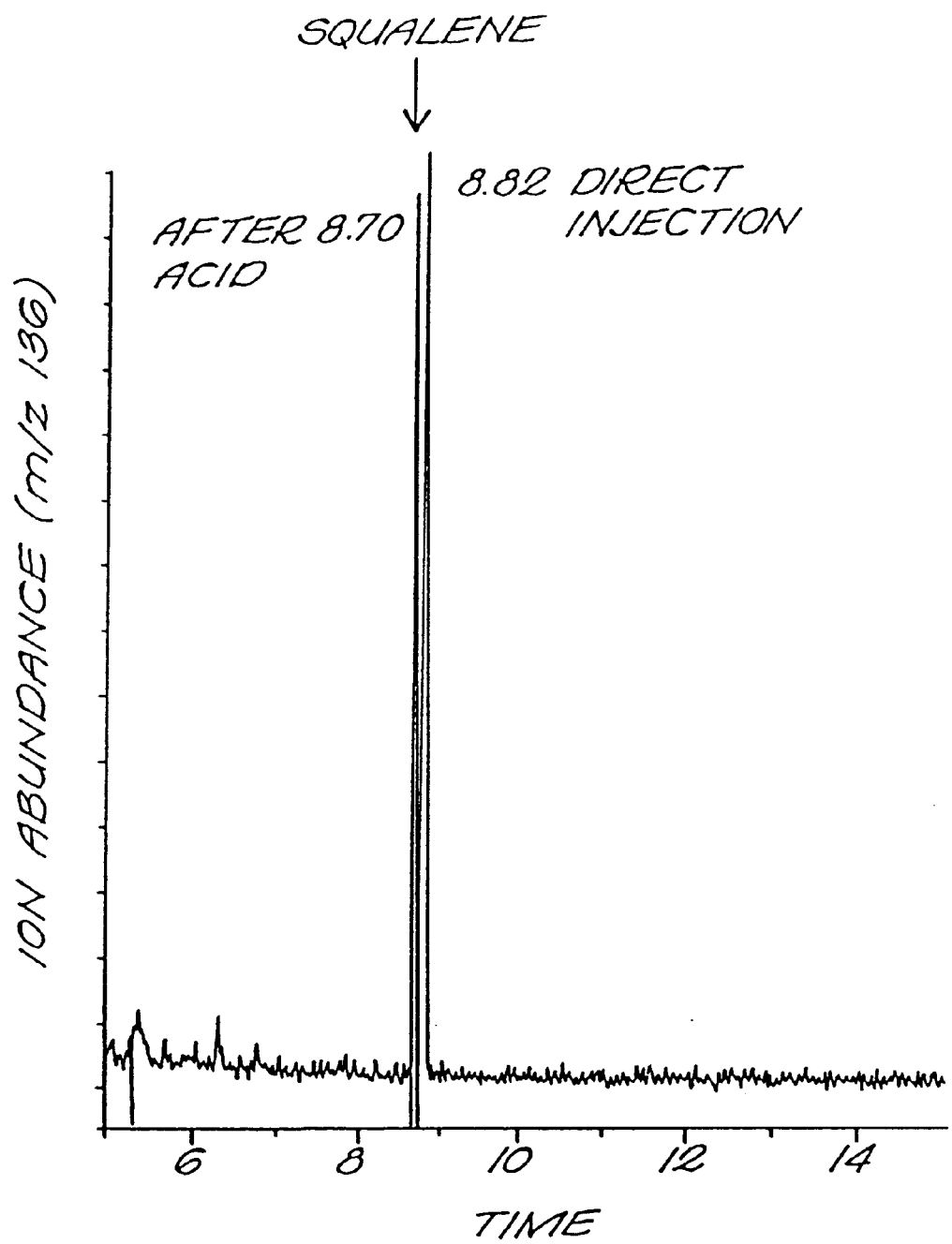
FIG. 2c shows acid-treated compound VI, having shifted to 8.70 min and the resultant mass spectrum now consistent with squalene.
Figure 2D:
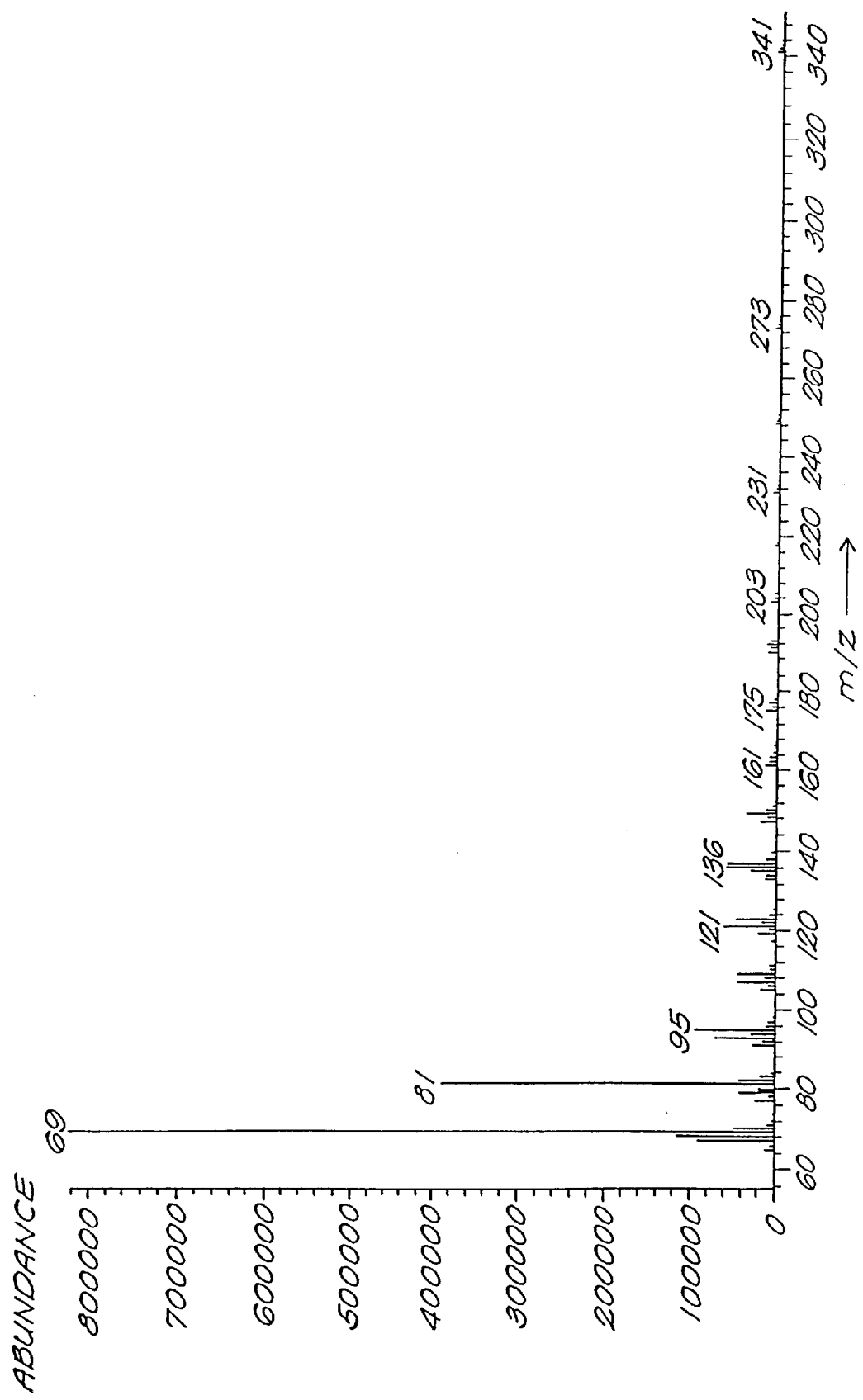
FIG. 2d shows preliminary GC/MS analysis of compound VI.

After TLC (as in FIG. 1C-c), compound VI was eluted with 1 ml mobile phase (chloroform:methanol:water 65:25:4, v/v)×4, brought to dryness under $N_2$, concentrated in hexane (2 µl) and taken to GC/MS (as in FIG. 2c under methods). Representative results (n=7) indicate a base peak of 69 [$(CH_3)_2CCHCH_2$] with prominent ions at repeating intervals of 68 [$CH_2C(CH_3)CHCH_2$] or 69: 136, 203, 273, 341, 410. The absence of a clear molecular ion (or M+−15) was noted. This fragmentation pattern is characteristic of isoprenoids (Farnsworth, C. C., Gelb, M. H. & Glomset, J. A. *Science* 247, 320–322 (1990); Popják, G., Edmond, J. Clifford, K. & Williams, V. J. *Biol. Chem.* 244, 1897–1918 (1969); Epstein, W. W. & Rilling, H. C. *J. Biol. Chem.* 245, 4597–4605 (1970), the teachings of which are incorporated herein by reference).

Figure 1E:
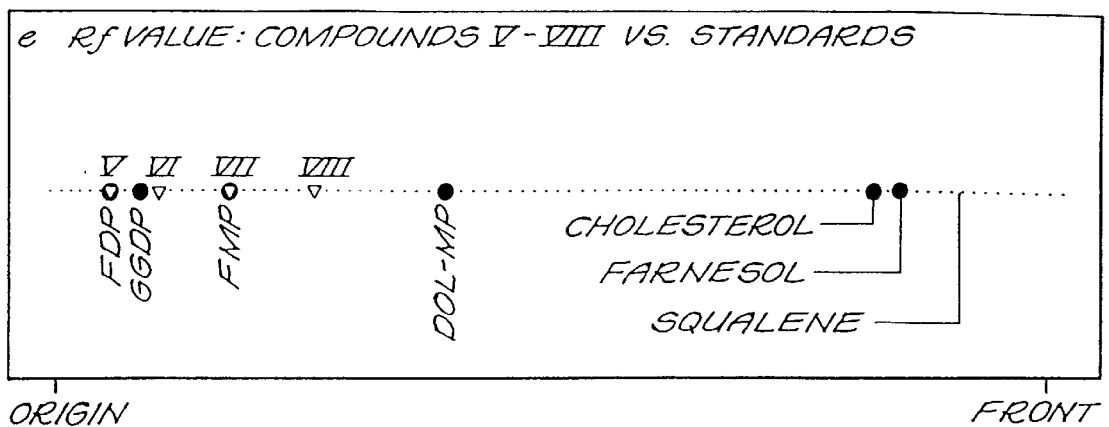
FIG. 1e is a comparison of compound V–VIII's Rf value with available standards.
Figure 1F:
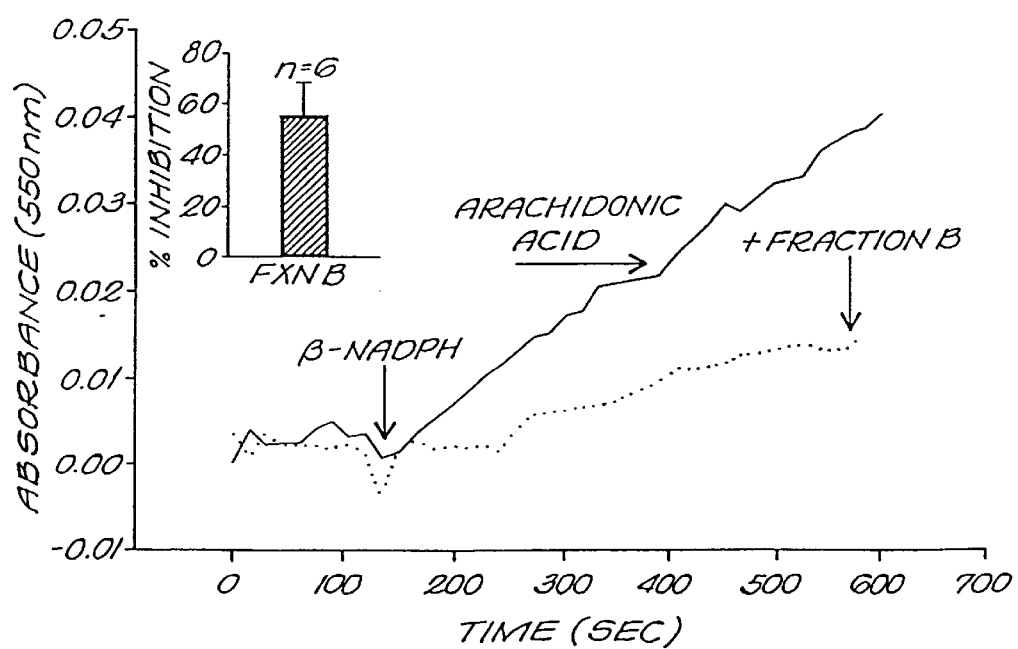
FIG. 1f shows a representative time course for Neutrophil Fraction B's inhibition of arachiodonic acid-stimulated superoxide anion generation.

For control purposes, Rf values were determined for available isoprenoids: isopentenyl diphosphate, geranyl diphosphate, geranylgeranyl diphosphate, dolichyl monophosphate, isoprenyl alcohols, squalene or cholesterol (FIG. 1e). Compounds V and VII (Rf values of 0.05±0.01 and 0.17±0.01) comigrated with farnesyl diphosphate (FDP) and farnesyl monophosphate (FMP), respectively. Compounds VI and VIII gave Rf values (0.10±0.01 and 0.25±0.02) identical to the TLC fractions with the most phosphorus/cell but different from available standards. Based on Rf values and the relationship between phosphorus content and mass (measured by scanning densitometry of charred TLC plates, Table 1g), compound VI contained two phosphates and compounds VII and VIII one phosphate. Together the results indicated the presence of four major non-saponifiable, phosphorylated lipids in neutrophils with chromatographic behavior consistent with polyisoprenyl phosphates.

FIG. 1g shows that after TLC of materials in Fraction B, plates were sprayed with molybdenum blue: 4.2M $H_2SO_4$ (1:1, v/v). Compounds containing phosphorus were quantitated first by scanning densitometry (Model PD and integration software, Molecular Dynamics, Inc.) and then by inorganic phosphorus determination (as in Chen, P. S. et al. *Anal Chem.* 28, 1756–1758 (1956), the teachings of which are incorporated herein by reference) after scraping, elution and concentration. Representative results are reported for compound VI, VII and VIII.

For further analysis of compounds VI and VIII and to substantiate the identification of compounds V and VII, each was isolated and subjected to GC/MS by direct injection or after conversion to $Me_3Si$ derivatives. All four lipids possessed the characteristic fragmentation pattern of isoprenoids (Farnsworth, C. C., Gelb, M. H. & Glomset, J. A. *Science* 247, 320–322 (1990), Table 2e). Compounds V and VII gave retention times and prominent ions also consistent with farnesyl diphosphate and farnesyl monophosphate which were confirmed by direct comparison to authentic samples (Table 2e). Compound VI gave a fragmentation pattern resembling that of squalene (molecular ion ($M^+$)= 410), yet anions m/z>410 were present and its retention was 0.10–0.12 min greater than that of squalene (FIGS. 2a & 2b). It is known that acid hydrolysis liberates 80% of the phosphate from polyisoprenyl diphosphates without substantial destruction of polyisoprenyl monophosphates (Van Dessel, G. A. F., Lagrou, A. R. Hilderson, H. J. J. & Dierick, W. S. H. In: CRC *Handbook of Chromatography* (eds Mukherjee, K. D., Weber, N. & Sherma, J.) 321–337 (CRC Press, Boca Raton, 1993)) and likewise led to the conversion of compound VI into a material with the retention and mass spectrum of squalene (FIGS. 2b & 2c). Compound VIII's retention and fragmentation pattern by GC/MS were very similar to that seen with compound VI; however compound VIII was not susceptible to acid hydrolysis. Molecular ions were not readily apparent for either compound VI or VIII; a trait consistent with GC/MS analysis of polyisoprenyl phosphates (Popják, G., Edmond, J. Clifford, K. & Williams, V. J. *Biol. Chem.* 244, 1897–1918 (1969) and Epstein, W. W. & Rilling, H. C. *J. Biol. Chem.* 245, 4597–4605 (1970)). Based on these physical properties, the proposed structures for compound VI and VIII were presqualene diphosphate (PSDP) (FIG. 2a) and presqualene monophosphate (PSMP), respectively.

In FIG. 2e, the structures of the four major phosphorylated, non-saponifiable neutrophil lipids were elucidated using several analytical techniques: (Serhan, C. N., Haeggström, J. Z. & Leslie, C. C. FASEB J. 10:1147–1158 (1996)) TLC (FIGS. 1d & e, mean±SEM, n≧15) to determine the compounds' Rf values relative to authentic dolichyl monophosphate (internal standard); (Weismann, G., Smolen, J. E. & Korchak, H. M. N. Engl. J. Med. 303, 27–34 (1980)) GC/MS for structural identification after direct injection, reaction (1:2 equivalents) with trimethylbromosilane in $CH_2Cl_2$ (RT, 2 hours) to generate trimethylsilyl (OTMS) derivatives ("NP"=not performed) or acid hydrolysis to monitor for the generation of squalene (FIGS. (2b)) and (3) quantitation by inorganic phosphorus determination (mean±SEM, n=3–5, d≧6) (19). Proposed structures were determined by comparison with authentic material when available.

In yeast, plants and mammalian liver, squalene synthetase condenses two molecules of farnesyl diphosphate to form the cyclopropylcarbinyl intermediate, presqualene diphosphate (PSDP), and in the presence of NADPH, squalene (Goldstein, J. L. & Brown, M. S. *Nature* 343, 425–430 (1990); Corey, E. J. & Volante, R. P. *J. Amer. Chem. Soc.* 98, 1291–1293 (1976); Mookhtiar, K. A., Kalinowski, S. S., Zhang, D. & Poulter, C. D. *J Biol. Chem.* 269, 11201–11207 (1994), the teachings of which are incorporated herein by reference). Alternatively, when reducing equivalents are depleted, yeast phosphates convert PSDP into presqualene monophosphate (PSMP) (Popják, G., Edmond, J. Clifford, K. & Williams, V. J. *Biol. Chem.* 244, 1897–1918 (1969)). Although human leukocytes biosynthesize both FDP and squalene, neither PSDP nor PSMP has been reported in neutrophils, which uniquely lack the mixed-function oxidases required to convert squalene to cholesterol (Shechter. I., Fogelman, A. M. & Popjak, G. *J. Lipid Res.* 21, 277–283 (1980), the teachings of which are incorporated herein by reference). Compounds V, VI, VII and VIII represented 0.1, 1.8, 0.4 and 0.5%, respectively, of the total phosphorylated lipid fraction (92.4) nmoles phosphorus/$10^7$ unstimulated PMN, n=3). Taken together, the results indicate that neutrophil non-saponifiable lipids include a series of biosynthetically-related polyisoprenyl phosphates.

Figure 3A:
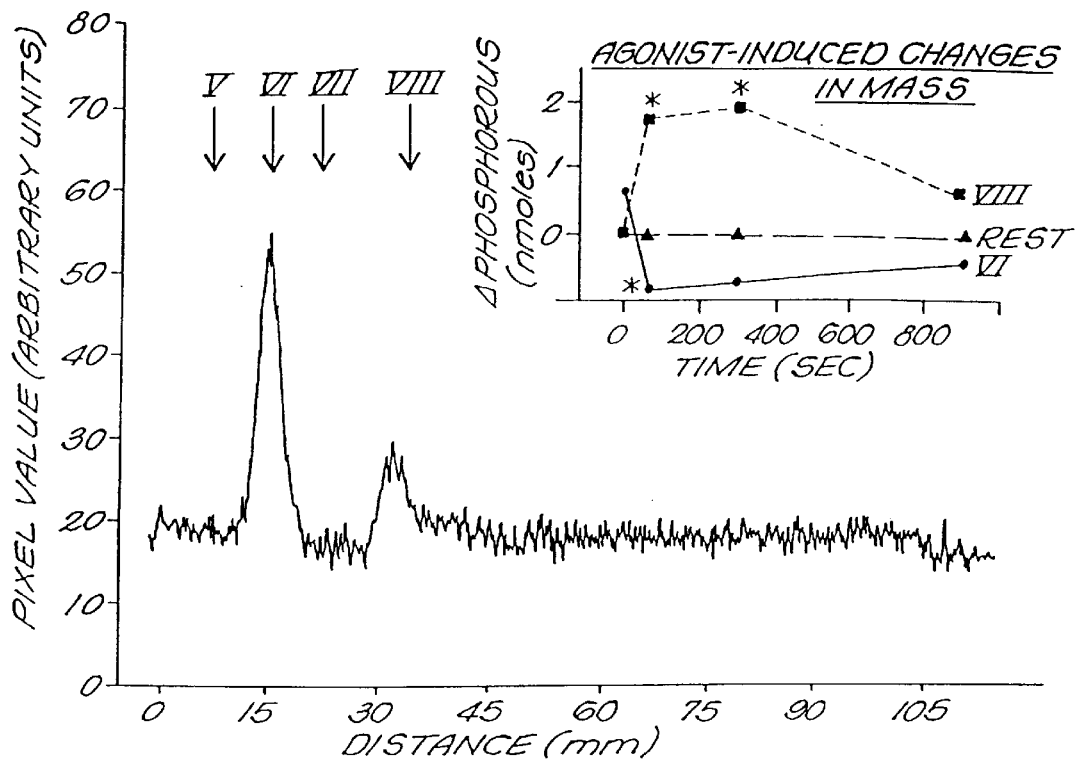
FIG. 3a is a representative phosphoimager profile of $^{32}$P-content after TLC of resting neutrophil extracts from cells incubated with $\gamma$-$^{32}$PO$_4$-ATP and (inset), time course for FMLP-stimulated changes in phosphorus content of compounds VI and VIII.

Resting neutrophils, exposed to $\gamma^{32}PO_4$-ATP to enable mass quantitation and identify phosphate turnover, selectively incorporated radiolabel into compounds VI and VIII (FIG. 3a). Exposure to the chemotactic peptide, FMLP, resulted in changes in compound VI and VIII's phosphorus content which were rapid (within 60 seconds), reciprocal (decrements in compound VI paralleled increments in compound VIII) and transient (FIG. 3a inset). FMLP stimulates neutrophil superoxide anion generation and increases carboxyl methylation of prenylated proteins via interaction with a G-protein-coupled, seven transmembrane-spanning receptor (Philips, M. R., Pillinger, M. H., Volker, C., Rosenfield, M. G., Weissmann, G. & Stock, J. B. *Science* 259, 977–980 (1992); Baggiolini, M., Boulay, F., Badwey, J. A. & Curnutte, J. T. FASEB J. 7, 10040–1010 (1993), the teachings of which are incorporated herein by reference). Decrements in the mass of compound VI paralleled the early increased rate of $O_2$- production with FMLP stimulation, which after approximately 5 minutes terminates as levels of compound VI return to baseline. These findings were consistent with a regulatory role for compound VI in NADPH assembly.

Cytokines prime leukocytes for inflammatory responses, including superoxide anion generation, by interacting with receptors whose signaling mechanisms remain to be fully elucidated (Gomez-Cambronero, J. & Sha'afi, R. I. in *Cell—Cell Interactions In The Release of Inflammatory Mediators.* (eds Wong, P. Y-K. & Serhan, C. N.) 35–71 (Plenum Press, New York, (1991), the teachings of which are incorporated herein by reference). Cytokine stimulation also regulates formation of compounds VI and VIII, as neutrophils are exposed to granulocyte/monocyte-colony stimulating factor (GM-CSF) which significantly increases $^{32}PO_4$ incorporation into both compounds VI (45.0%) and VIII (84.1%) (FIG. 3b) without statistically significant changes in mass by inorganic phosphorus determination (n=3). Together these results indicate that compounds VI and VIII are biosynthetically related, and that neutrophil activation by different classes of receptors stimulates the incorporation of $^{32}PO_4$ into these lipids.

To test the impact of compounds VI and VIII on neutrophil responses, the isolated lipids were introduced into neutrophils by electroporation prior to determining NADPH oxidase activity. In nM-$\mu$M quantities, compound VI resulted in 60% inhibition of the FMLP-triggered generation of superoxide anion, while $O_2$- production in the presence of compound VIII was unaltered (FIG. 4a). At these concentrations, neither compound VI nor VIII alone stimulated $O_2$- production (FIG. 3c). Prenyl cysteine analogues can disrupt G-protein interaction with activated FMLP receptors (Scheer, A. & Gierschik, P. *Biochemistry.* 34,4952–4961 (1995), the teachings of which are incorporated herein by reference); therefore to determine compound VI's level of action, neutrophil superoxide anion generation was examined in the presence of phorbol 12-myristate 13-acetate (PMA), a potent trigger for $O_2$- production which bypasses cell surface receptors to stimulate protein kinase C and subsequent NADPH assembly (see for example, Baggiolini, M., Boulay, F., Badwey, J. A. & Curnutte, J. T. FASEB J. 7, 10040–1010 (1993); FIG. 3c). Compound VI (1 $\mu$M) inhibited PMA (100 $\eta$M) activated superoxide anion generation by 44% in a concentration-dependent fashion with significant inhibition still present at 10 nM (FIG. 4b, inset). PMA-stimulated $O_2$- production was not significantly influenced by either compound VIII or other related eicosanoids (FIG. 4b). These results indicate that compound VI selectively inhibits $O_2$- production at a site down-stream from G-protein-receptor interactions.

FIG. 3c shows neutrophils ($10^7/500$ $\mu$l) that were electroporated (as in FIGS. 4, 4a and 4b) in the presence of 0.2% ethanol. After electroporation, cells in cytochrome c (0.7 mg/ml) were exposed (10 min, 37° C.) to PMA ($10^{-7}$ M), FMLP ($10^{-7}$ M) plus cytochalasin b (15 $\mu$g/ml), compound VI (1 $\mu$M) or compound VIII (1 $\mu$M) and supernatants monitored at 550 nm. Values represent the mean±SEM for n≧4.

Since leukocyte adhesion and diapedesis are also critical early events in inflammation (reviewed in Serhan, C. N., Haeggström, J. Z. & Leslie, C. C. FASEB J. 10:1147–1158 (1996) and Baggiolini, M., Boulay, F., Badwey, J. A. & Curnutte, J. T. FASEB J. 7, 10040–1010 (1993), the impact of polyisoprenyl phosphates on neutrophil homotypic adhesion was evaluated with intact, freshly isolated cells. Here too, exposure to $\mu$M levels of compound VI but not compound VIII resulted in significant inhibition (63%, p<0.001) of the aggregatory response to FMLP (FIGS. 4c and d), while neither compound VI nor VIII alone stimulated adhesion. In addition, calcium mobilization by 1,4,5-inositol triphosphate ($IP_3$) is important in neutrophil activation and cytokine signal transduction (Weismann, G., Smolen, J. E. & Korchak, H. M. N. Engl. J. Med. 303, 27–34 (1980) and Gomez-Cambronero, J. & Sha'afi, R. I. in *Cell—Cell Interactions In The Release of Inflammatory Mediators.* (eds Wong, P. Y-K. & Serhan, C. N.) 35–71 (Plenum Press, New York, (1991)). Compound VI (1 $\mu$M) also inhibited FMLP-triggered $IP_3$ formation (56%, FIG. 4e). These findings indicated that compound VI inhibits agonist-induced neutrophil responses that are relevant during host defense.

Figure 4A:
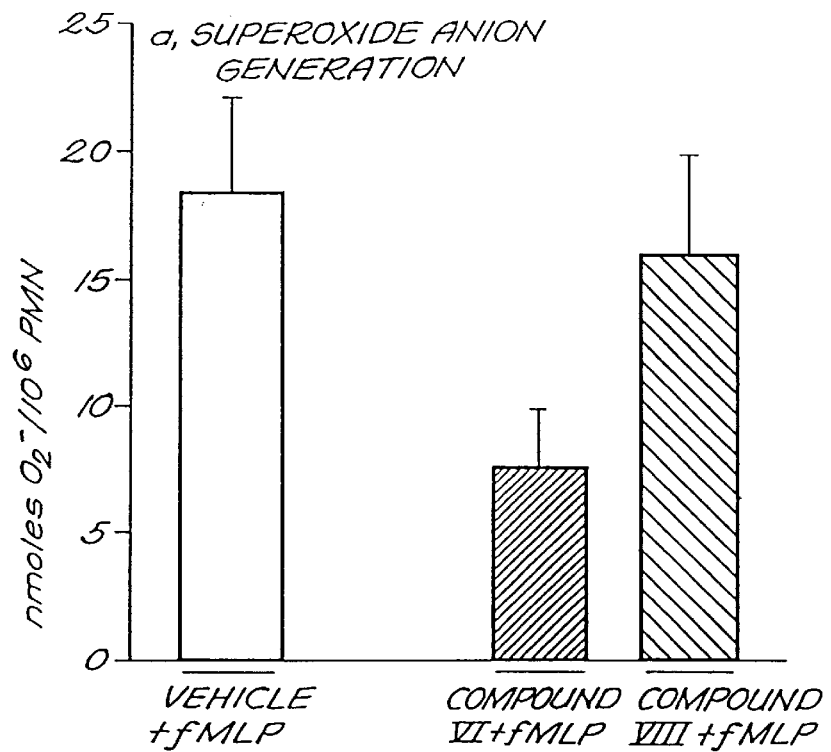
FIG. 4a is a graph of FMLP-stimulated superoxide anion generation with electroporated neutrophils in the presence of compounds VI and VIII.
Figure 4B:
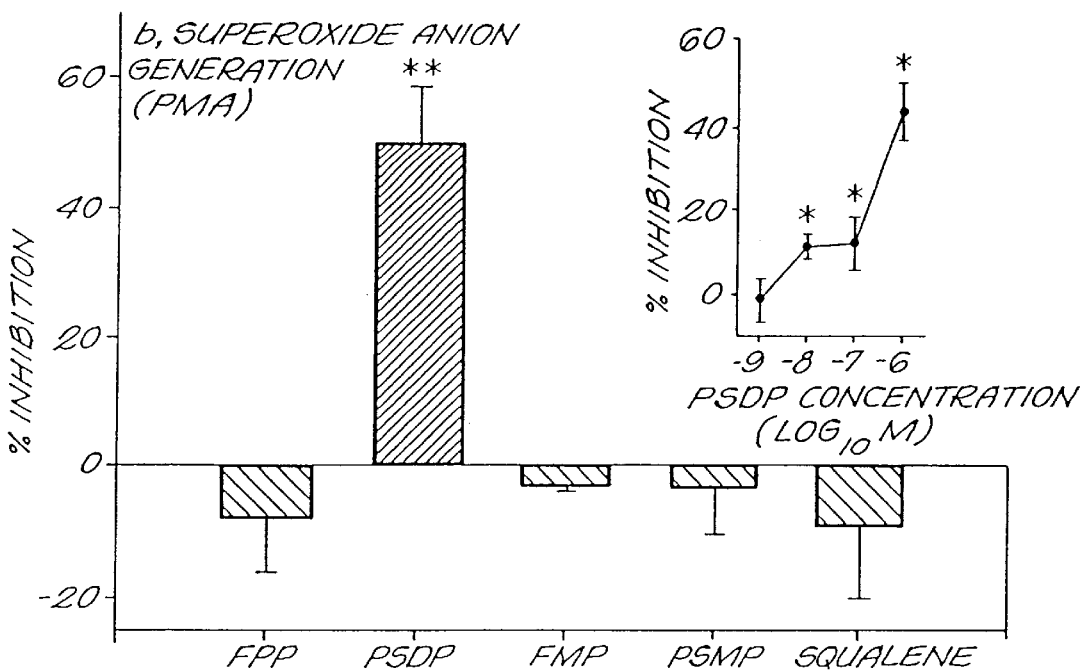
FIG. 4b is a graph of PMA-stimulated superoxide anion generation with electroporated neutrophils in the presence of compound VI and related isoprenoids and dose response (b inset) of compound VI's inhibition of $O_2$- production.
Figure 4C:
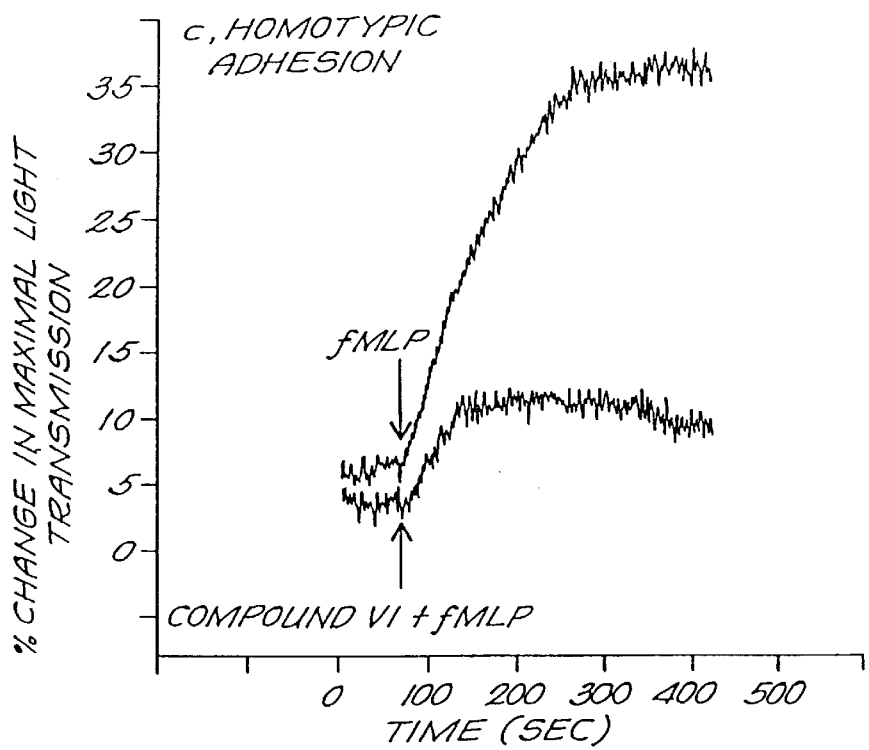
FIG. 4c is a representative tracing of neutrophil homotypic adhesion.
Figure 4D:
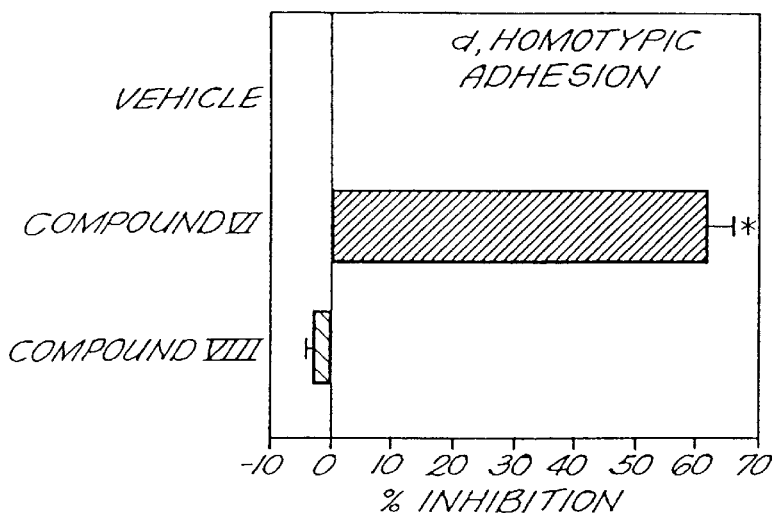
FIG. 4d shows the % inhibition of FMLP-stimulated homotypic adhesion.
Figure 4E:
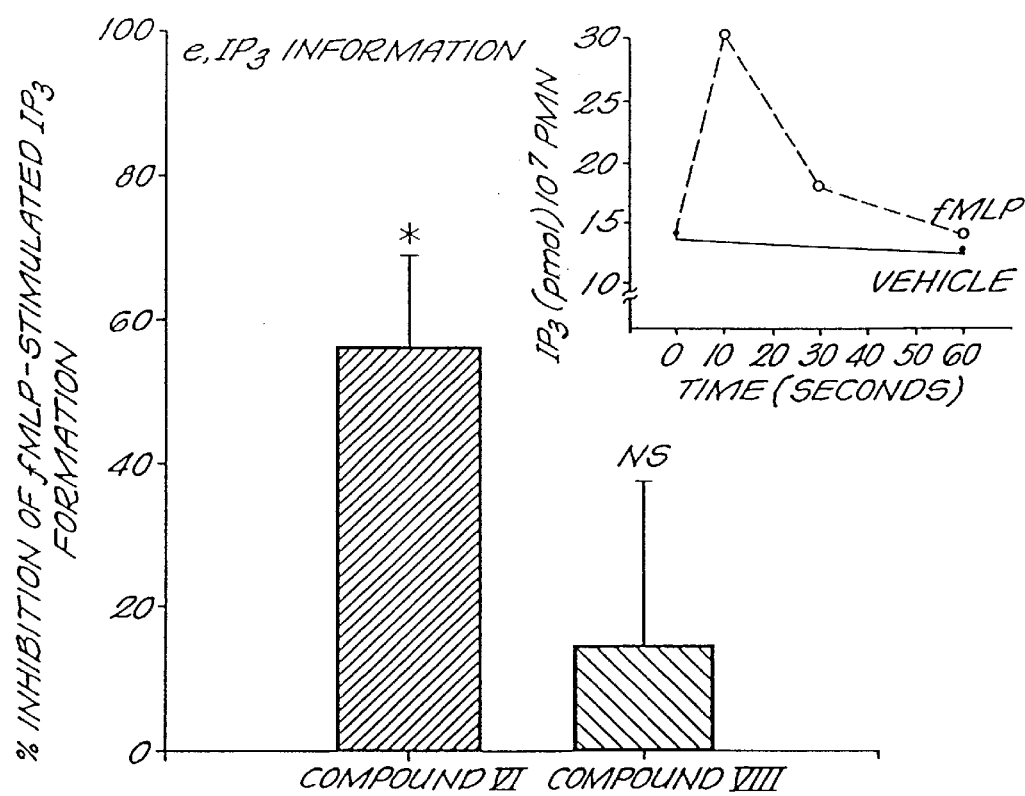
FIG. 4e, shows the % inhibition of FMLP-stimulated IP$_3$ formation.
Figure 4F:
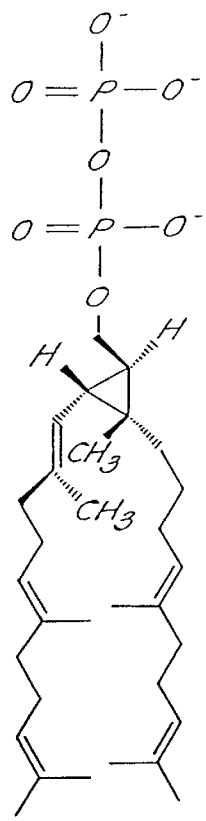
FIG. 4f, is a proposed scheme for polyisoprenyl phosphate regulation of neutrophil responses.
Figure 4F:
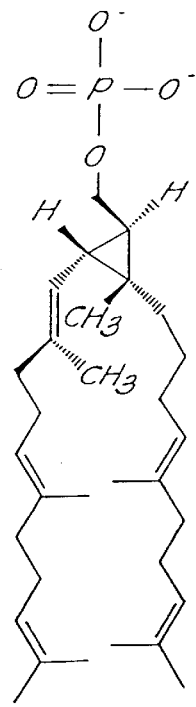

Isoprenoids are pivotal intermediates in the generation of diverse classes of compounds including serols, retinoids, dolichols, ubiquinone and prenylated proteins (Adair, W. L. & Keller, R. K. Methods Enzymol. 111, 201–215 (1985); Goldstein, J. L. & Brown, M. S. *Nature* 343, 425–430 (1990); Quinn, M. T. J. *Leukoc. Biol.* 58, 263–276 (1995), the teachings of which are incorporated herein by reference). Here, the major polyisoprenyl phosphates in neutrophils have been indentified. In response to receptor activation, presqualene diphosphate and presqualene monophosphate rapidly remodel, and presqualene diphosphate regulates relevant cellular bioactions (FIG. 4f). Together our results indicate that these compounds represent potent, novel lipid-derived signals and provide evidence for an intracellular signaling role for isoprenoid remodeling.

Neutrophil lipids (isolated from human neutrophils from purified periperal blood of healthy donors) (FIG. 1) were saponified (10% KOH in methanol, 37° C., 30 min), extracted (as described generally in Van Dessel, G. A. F., Lagrou, A. R. Hilderson, H. J. J. & Dierick, W. S. H. In: *CRC Handbook of Chromatography* (eds Mukherjee, K. D., Weber, N. & Sherma, J.) 321–337 (CRC Press, Boca Raton, 1993)) and separated by CC4 silica (1 gm/$10^8$ PMN) chromatography with sequential elutions of chloroform:methanol (2:1, v/v) (Fraction A) and chloroform:methanol:water (10:10:3, v/v) (Fraction B).

FIGS. 1a–e represent neutrophil-derived non-saponifiable phospholipids which regulate the generation of superoxide anion by neutrophil sonicates. Eluents were evaporated under vacuum, concentrated in ethanol and either (FIGS. 1a–c) added to incubations for superoxide anion generation or (FIGS. 1c–e) spotted on TLC plates for development (50 min, 25° C.) in an environment saturated with chloroform:methanol:water (65:25:4, v/v).

To determine $O_2^-$ production (FIGS. 1a–c), post-nuclear supernatants from neutrophils after sonication (0.1–0.5 mg protein/ml) (as generally described in Bromberg, Y. & Pick, E. *Cell. Immunol.* 88, 213–221 (1984), the teachings of which are incorporated herein by reference), 100 $\mu$M phosphatitic acid (C10:0, Avanti Polar Lipids, Inc.) and lipid extracts (0.1% ethanol) were added to cytochrome c (60 $\mu$M), sucrose (170 mM), EGTA (1 mM), FAD (10 $\mu$M), $NaN_3$ (2 mM) and either superoxide dismutase (30 ug/ml) or $H_2O$ at 0° C. (as in 20). After 2 min (37° C.) in a thermal-jacketed cuvette, B-NADPH (200 $\mu$M) was added to initiate reactions and absorbance (550 nm) was monitored at 15 second intervals or following termination (10 minutes, 0° C.).

For screening of Fraction B by TLC, sequential 5 mm segments of each lane were scraped, eluted with 1 ml×4 of chloroform:methanol (2:1) and brought to dryness under $N_2$. Inorganic phosphorus levels were quantitated as in described in Chen, P. S. et al. *Anal. Chem.* 28, 1756–1758 (1956).

Prior to densitometry, TLC plates with material run in parallel were either stained with iodine, sprayed with 10% $CuSO_4$ in 8% phosphoric acid and charred (100° C., 20 min followed by 120° C., 10 min) (as described generally in Tou, J. & Dola, T. *Lipids* 30, 373–381 (1995), the teachings of which are incorporated herein by reference) or sprayed directly with molybdenum blue: 4.2 M sulfuric acid (1:1, v/v).

Rf values for authentic FDP, geranylgeranyl diphosphate (GGDP), dolichyl monophosphate (DOL-MP), cholesterol, farnesol, squalene (Sigma Chemical Co.) and FMP (American Radiolabeled Chemicals, Inc.) are indicated for comparison. Compounds VI, VII and VIII frequently ran as doublets suggesting the presence of isomers or closely related compounds in each major peak.

The isolation and elucidation of phosphorylated non-saponifiable neutrophil lipids are depicted by FIGS. 2 (a–c). Specifically, GC/MS of compound VI before and after acid hydrolysis shows a mass spectrum of compound VI consistent with presqualene diphosphate with a limited ion chromatogram for m/z 136 (i.e., 2 internal isoprene units) after direct injection. Acid-treated compound VI was found to shift to 8.70 min and had a mass spectrum now consistent with squalene.

After quantitation by phosphorus determination, ~500 ng/compound in hexane (2 $\mu$l) was injected into GC/MS (Hewlett-Packard Co., Model 5890 GC and 5781A MS). To enhance detection, $Me_3Si$-derivatives were produced by treatment with BSTFA (N,O-bis(trimethylsiyl) trifluoroacetamide), or compounds were subjected to acid (0.01 N HCl in 50% methanol, pH 2.0@100° C., 20 min) to liberate pyrophosphate when present. Diagnostic ions in (FIG. 2a), namely m/z 489 (M-96), 447 M-[96-C($CH_3$)$_2$], 410 M-($HP_2O_7$), 341 [($HP_2O_7$)-(C($CH_3$)$_2$CHCH$_2$)], 273 M-[($HP_2O_7$)-69-($CH_2$C($CH_3$)CHCH$_2$)], 205 M-[($HP_2O_7$)-69-($CH_2$C($CH_3$)CHCH$_2$×2)], 136 ($CH_2$C($CH_3$)CHCH$_2$×2], 95 [C($CH_3$)$_2$CH($CH_2$)$_2$C], 81 [($CH_2$C($CH_3$)CH($CH_2$)$_2$)-$H^+$], and 69 [base peak; ($CH_3$)$_2$CCHCH$_2$] were consistent with presqualene diphosphate, and in (FIG. 2c), squalene (Popják, G., Edmond, J. Clifford, K. & Williams, V. J. *Biol. Chem.* 244, 1897–1918 (1969), Epstein, W. W. & Rilling. H. C. *J. Biol. Chem.* 245, 4597–4605 (1970)).

PMN (20×$10^6$/ml in $PO_4$-free HBSS (Hanks buffered saline solution) were labeled with $\gamma$-$^{32}PO_4$-ATP (40 $\mu$Ci/ml, 90 min, 37° C.), and saponified (10% KOH in methanol, 30 min, 37° C.). Non-saponifiable lipids were extracted and separated by one-dimensional TLC (chloroform:methanol:water (65:25:4 (v/v), 50 min, RT). $^{32}$P content was determined by phosphoimager (Model 425E and integration software, Molecular Dynamics, Inc.) (O=origin). Because destruction of the TLC plate was not required for $^{32}$P analysis, the same lane was later exposed to iodine vapor and the corresponding Rf values for compounds V–VIII are demonstrated for the purposes of comparison (representative of n=6, d=12). To determine FMLP ($10^{-7}$ M)-induced changes in compound VI and VIII mass (inset), radioactive compounds were eluted and inorganic phosphorus levels were measured. In addition, PMN labeled with $\gamma$-$^{32}PO_4$-ATP were incubated in the presence or absence of GM-CSF (25 ng/ml, 60 min, 37° C.)(b) with $^{32}$P content quantitated as above. Values represent the mean±SEM for duplicate determinations from at least two separate PMN. The percent increase after exposure to GM-CSF is relative to parallel incubations with cells in the absence of agonist. **p<0.0005 and * p<0.03 by Student's paired t-test.

Figure 3B:
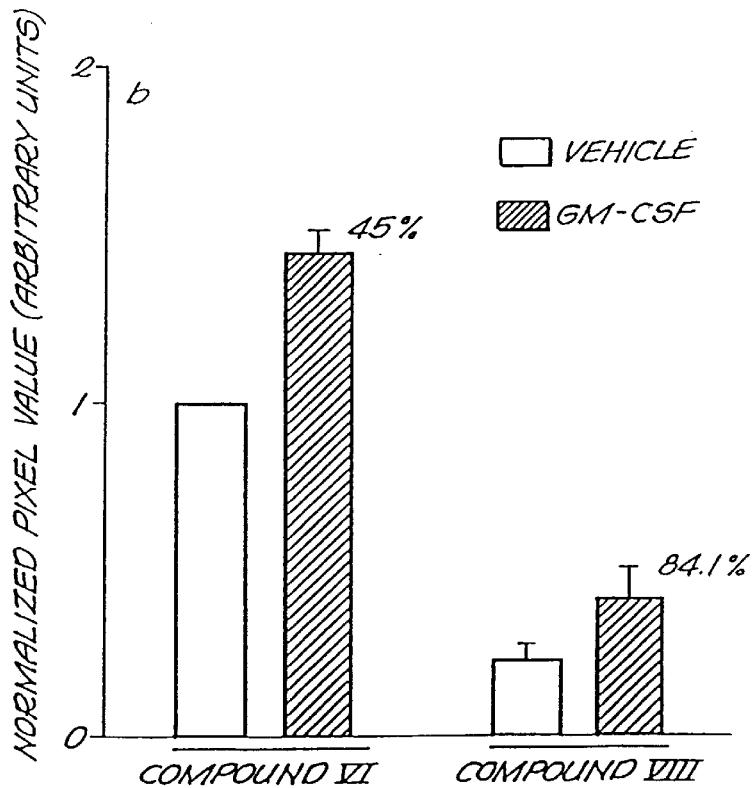
FIG. 3b depicts the impact of GM-CSF on $^{32}$PO$_4$ incorporation into compounds VI and VIII.
Figure 3C:
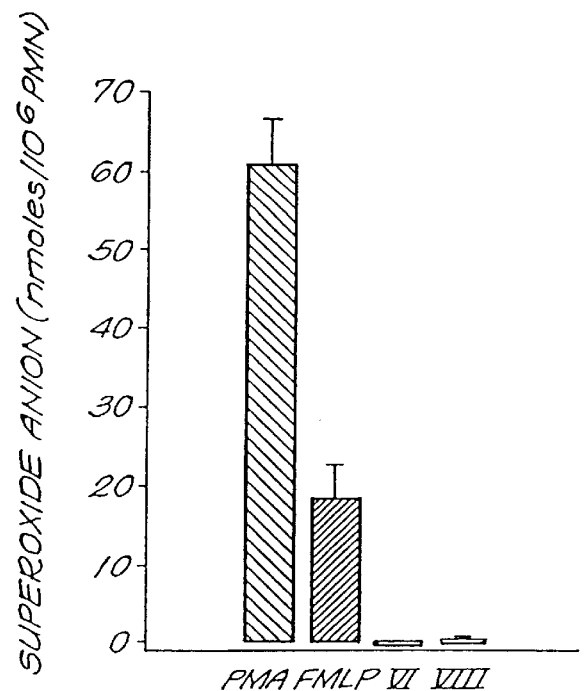
FIG. 3c depicts superoxide anion generation by electroporated neutrophils.

FIGS. 3a–e represent neutrophils which incorporate $^{32}$PO4 into non-saponifiable lipids; receptor activation triggers incorporation and turnover in compounds VI and VIII. For example, FIG. 3a depicts a representative phosphoimager profile of $^{32}$P-content after TLC of resting neutrophil extracts from cells incubated with $\gamma^{32}$PO$_4$-ATP and (inset), time course for FMLP-stimulated changes in phosphorus content of compounds VI and VIII. FIG. 3b shows the impact of GM-CSF (b) on PO$_4$ incorporation into compounds VI and VIII.

FIGS. 4a–f demonstrate how compound VI selectively inhibits neutrophil responses.

Impact of compounds VI and VIII and related isoprenoids on (FIG. 4a) FMLP and (FIG. 4b) PMA-stimulated superoxide anion generation with electroporated neutrophils and dose response (b. inset) of compound VI's inhibition of O$_2$-production. FIG. 4c is a representative tracing of neutrophil homotypic adhesion. FIG. 4d shows the % inhibition of FMLP-stimulated homotypic adhesion and FIG. 4e, IP$_3$ formation. FIG. 4f is a proposed scheme for polyisoprenyl phosphate regulation of neutrophil responses.

Neutrophils (10$^7$/500 µl) were electroporated (1.65 kV/cm, 250 µF, Ω∞, Invitrogen Electroporator VI) at 0° C. in the presence of 10$^{-9}$–10$^{-6}$ M compound VI, VIII, FDP, FMP, squalene or vehicle (ethanol 0.2%). After electroporation, cells, in cytochrome c (0.7 mg/ml), were exposed (10 minutes, 37° C.) to either cytochalasin b (5 µg/mL) and FMLP (10$^{-7}$ M)(a) or PMA ((10$^{-7}$ M)(b) and supernatants monitored at 550 mm. Electroporation gave a 49.9% reduction in FMLP-stimulated NADPH oxidase compared to naive cells. Values (FIGS. 4a and 4b) represent the mean±SEM for n≧3, d≧6. For adhesion (FIGS. 4c and 4d), changes in light transmittance were monitored (as in Fiore, S., Nicolaou, K. C., Caulfield, T., Kataoka, H. & Serhan, C. N. Biochem. J. 266, 25–31 (1990), the teachings of which are incorporated herein by reference) after addition of compounds VI, VIII (1.6 µM) or vehicle (0.5 min) and FMLP (0.5–5 µM) (2.5 min). Cell viability remained>99%. Values represent the mean±SEM for n=3, d=9. 1,4,5-inositol-triphosphate levels were determined (Amersham) in fresh PMN (10$^7$ cells) exposed (5 minutes, 37° C.) to compound VI, compound VIII (1 µM) or vehicle and stimulated with FMLP (10$^{-7}$M, 37° C.) (as in FIG. 4e). % Inhibition after 10 second exposure to FMLP is reported as mean±SEM for n=4, d≧8. *p <0.05 in Student's paired t-test compared with control, while "NS" indicates no significant change compared to incubations in the presence of vehicle (ethanol 0.2%) alone. Stereochemistry of PSDP and PSMP (FIG. 4f) were assigned by routine methods (Poulter, C. D. and Rilling, H. C. Acc. Chem. Res. 11, 307–313, (1978), the teachings of which are hereby incorporated by reference).

Figure 5:
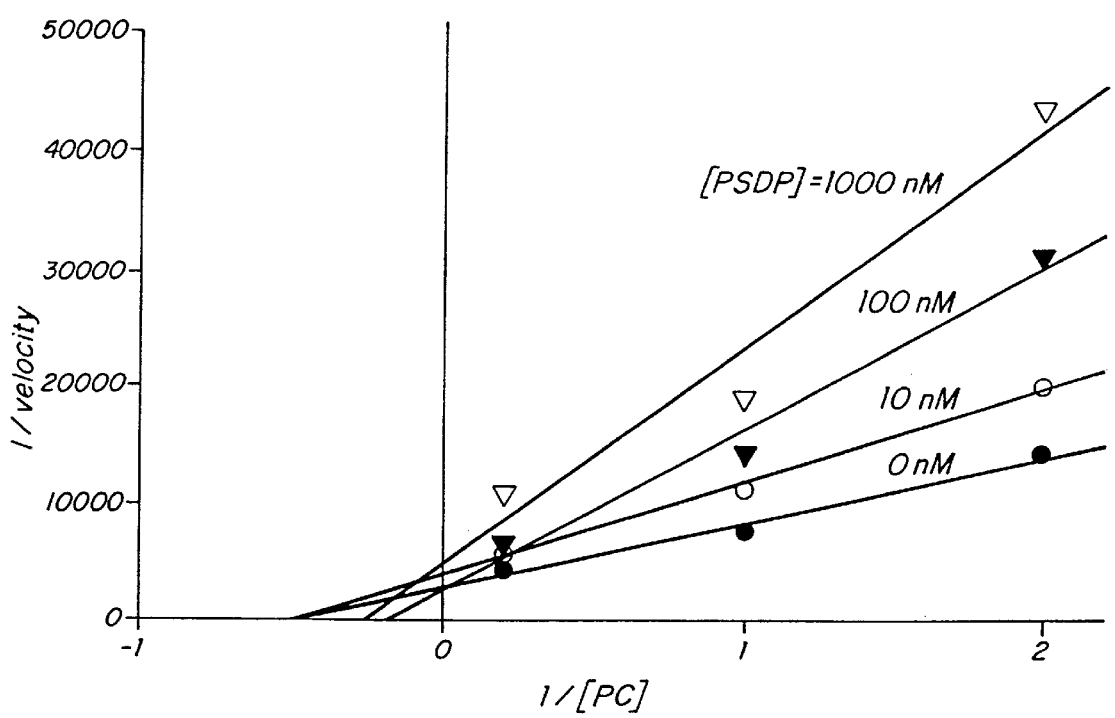
FIG. 5 shows the inhibition of phospholipase D by PSDP at several concentrations.

Phospholipase D (PLD) plays a central role in cellular activation in diverse cell types via the release of the bioactive fatty acid, phosphatidate. Several agonists operating through different classes of receptors have been defined that stimulate cellular PLD activity. No known endogenous regulators of PLD have been identified. Activation of neutrophils leads to an increase in intracellular phosphatidic acid that is generated predominantly via the hydrolysis of phosphatidyl choline by phospholipase D (Agwu, DE, et al., Journal of Clinical Investigation 1991; 88:531). Because PSDP inhibited phosphatidate mediated superoxide anion generation in human neutrophil sonicates (Levy, BD, et al., Nature 1997; 389:985), its impact on phospholipase D was determined. A purified enzyme was utilized to directly evaluate the action of PSDP with PLD. Lineweaver-Burk plots for PLD (3 units/125 µL; EC 3.1.4.4, Sigma Chemical Co.) in the presence of EtOH (0.2%) or increasing concentrations of PSDP are reported in FIG. 5. After addition of PSDP to PLD (5 min, 30° C.), phosphatidyl choline (lecithin) in 60 mM Tris/HCl+10 mM CaCl$_2$, pH 7.5 was added (30° C.) and reactions were terminated at 30 second intervals (t0–90 sec) with Tris-HCl (1 M) plus EDTA (50 mM). Choline release was quantitated as in Abousalham A. et al. Biochimica et Biophysica Acta 1;1158 (1993). For PLD, the Vmax was 2.49 nmoles choline/sec and the Km was 3.62 mM (n≧3, d≧2). PSDP inhibited this enzyme and gave a Ki<100 nM. These results indicate that PSDP is a potent inhibitor of PLD and suggest that the mechanism for the inhibition, based on the L-B analysis, is competition for the enzyme's substrate. In addition, this assay is ideally suited to screen novel polyisoprenyl phosphate analogs for bioactivity.

In addition to PLD, phospholipase C plays a critical role in intracellular signaling via the hydrolysis of inositol lipids to diacyl glyceride (DAG) and inositol trisphosphate (IP$_3$) to effect a cascade of cellular events in response to pro-inflammatory stimuli. DAG activates protein kinases and is converted, in part, to phosphatidic acid by DAG kinase. Therefore, PLC together with DAG kinase provides a second major source of phosphatidic acid in human neutrophils (Agwu, DE, et al., Journal of Clinical Investigation 1991; 88:531). Because of PLC's participation in phosphatidate formation, PSDP was analyzed to determine whether it also inhibited this enzyme's activity. To this end, the impact of PSDP on fMLP-stimulated IP$_3$ formation as a surrogate for phospholipase C activity was examined (FIG. 4e). Incubation (5 min. 37° C.) of freshly isolated human neutrophils (10×10$^6$) with PSDP (1 µM) just prior to exposure to fMLP (100 nM) resulted in >50% inhibition of IP$_3$ levels 10 seconds after exposure to an agonist (time to peak formation in these cells) as determined using a D-myo-inositol 1,4,5-trisphosphate[$^3$H]-based assay (Biotrak radioimmunoassay system, Amersham Life Science #TRK 1000).

Figure 6:
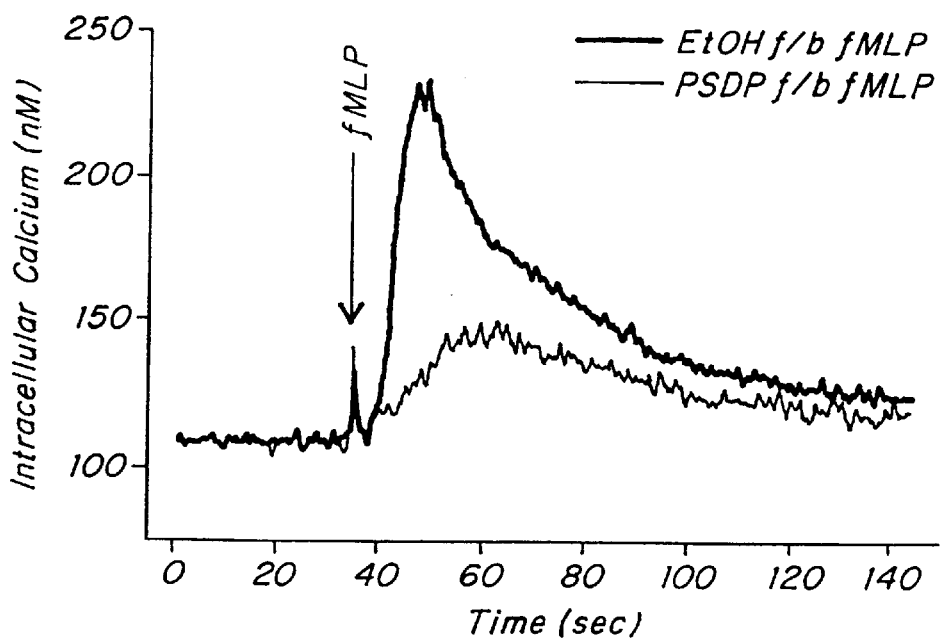
FIG. 6 shows the inhibition of fMLP-stimulated [Ca$^{+2}$] mobilization.
Figure 7:
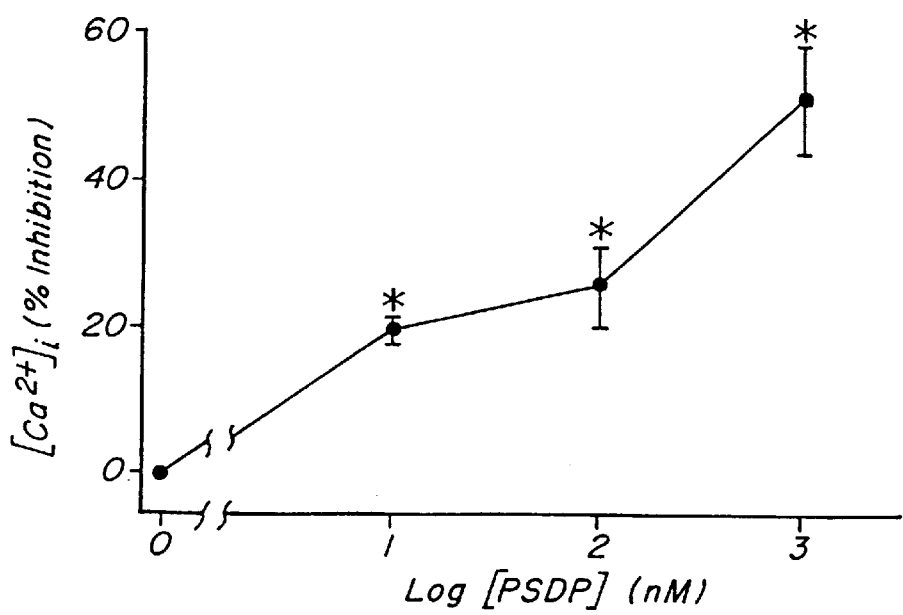
FIG. 7 shows the concentration dependence of inhibition of fMLP-stimulated [Ca$^{+2}$] mobilization.

Inositol trisphosphate is known to be an important intracellular mediator of calcium mobilization from intracellular stores, a critical event in cellular activation (Exton, JH, Annual Review of Pharmacology and Toxicology 1996; 36:481). In order to determine the functional importance of the PSDP-mediated reduction in IP$_3$ levels, fMLP-stimulated intracellular calcium mobilization in the presence of polyisoprenyl phosphates was measured. FURA-2 (1 µM) loaded neutrophils (10×10$^6$/2 ml) in the presence of EDTA (5 mM) were exposed (5 min, 37° C.) to PSDP (10$^{-5}$–10$^{-6}$ M) or EtOH (0.1%), followed by 1 nM fMLP. FIG. 6 shows a representative incubation demonstrating inhibition by PSDP (1 µM) of fMLP-stimulated [Ca$^{2+}$]$_i$ mobilization. This inhibition was concentration dependent FIG. 7 and significant (n=3, mean±SEM, *P<0.05 by Student's t-test). Together these results indicate that in addition to phospholipase D, PSDP also inhibits PLC activity and that this assay can be utilized to screen novel polyisoprenyl phosphate analogues for bioactivity.

Figure 8:
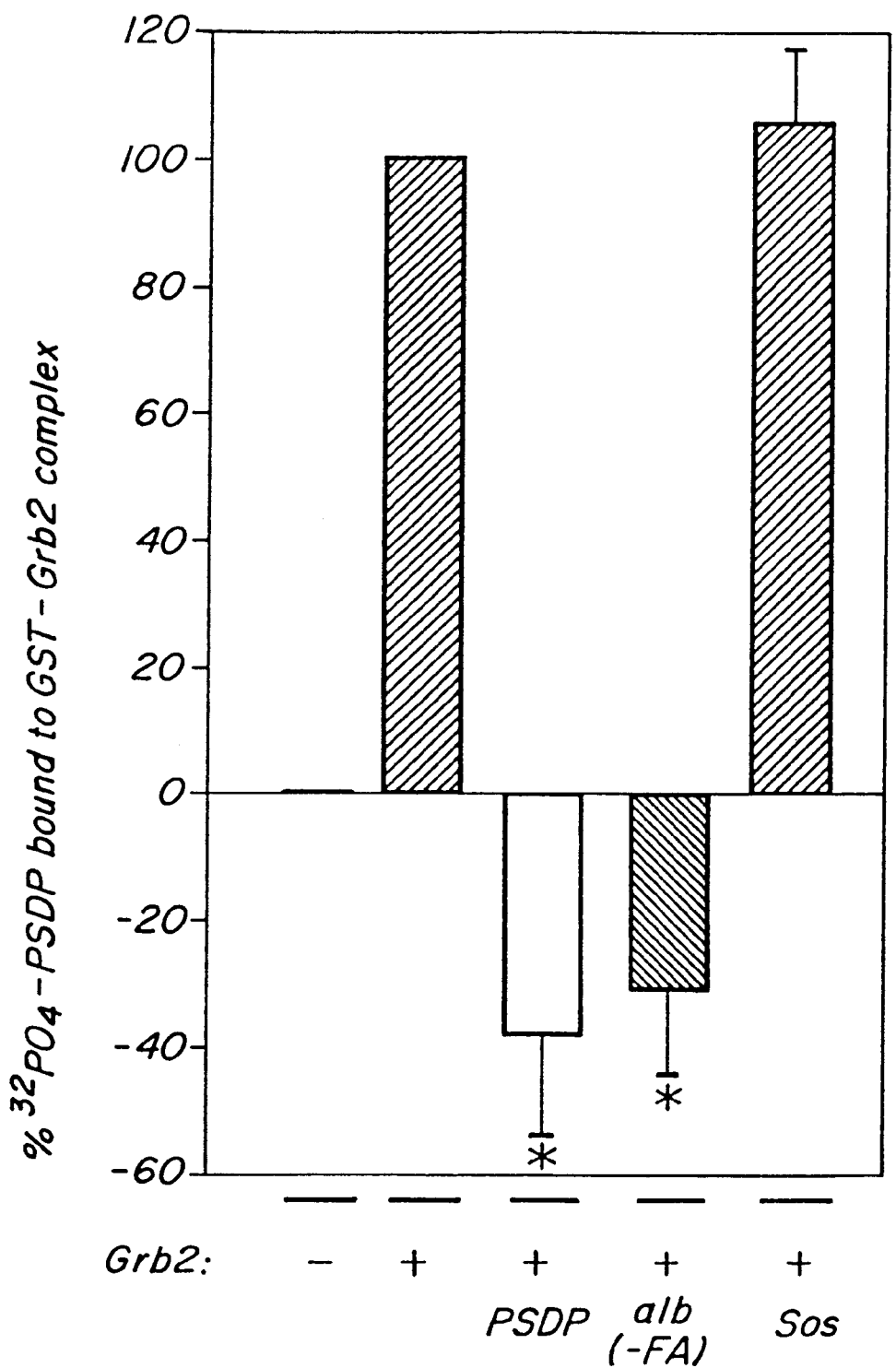
FIG. 8 demonstrates that presqualene diphosphate associates with Grb2 SH2 domains.

SH2 and SH3 domains on intracellular proteins are thought to be critical sites of phosphorylation by specific kinases in the regulation of signal transduction (Pawson, T., Schlessinger, J., Current Biology, 1993; 3:434). Of special interest during inflammation and wound repair, these domains appear to play pivotal roles during cytokine (e.g., growth factors) signaling via tyrosine kinases. Granulocyte/macrophage-colony stimulating factor stimulates phosphate turnover in presqualene diphosphate and presqualene monophosphate (FIG. 3b) indicating a potential role for these compounds in cytokine signaling. Furthermore, SH2 or SH3 domains are present on important regulatory intracellular enzymes (e.g., PLCγ) and have been reported to play pivotal roles in neutrophil responses (e.g., NADPH oxidase activation) (Ree, SG, et al., *Journal of Biological Chemistry*, 1997; 272:15045) (McPhail, LC, *Journal of Experimental Medicine*, 1994; 180:2011) Therefore, it was determined whether polyisoprenyl phosphates could associate with these important intracellular phosphate-sensing domains. Equilibrium binding was determined for $^{32}PO_4$-PSDP (1 μM) to the adaptor protein, Grb2, which is known to carry two SH3 domains and one SH2 domain (Lowenstein, EJ, et al., *Cell*, 1992; 70:431). Radiolabeled PSDP bound to a Gst-Grb2 fusion protein complexed to agarose beads (Upstate Biotechnology #14–128) after incubation for 20 min at 37° C. Bound material was separated from unbound by spin filtration (0.2 μm) and quantitated by scintillation counting. The radioligand could be competed off Gst-Grb2 by excess unlabeled PSDP or delipidated albumin (50 μg), but not by the SH3 containing peptide, Sos (50 μg) (FIG. 8; n=3, mean±SEM, *P<0.01). These results indicate that PSDP can associate with SH2 domains and suggests another potential intracellular target for this novel messenger. In addition, these studies define a novel screening assay for association of phosphorylated lipids with protein phosphate-sensing domains in lipid-protein interactions.

V. Utilities

The compounds of this invention have the biological activity of natural PSDPs, but are more resistant to degradation or alternatively inhibit the degradation of natural PSDPs. The disclosed compounds therefore have utility as pharmaceuticals for treating or preventing a number of diseases or conditions associated with inadequate or inappropriate inflammatory mediated cellular response in a subject.

Also encompassed by this invention is a method of screening PSDP analogs or other compounds to identify those having a longer tissue half-life than the corresponding natural PSDP. This method can be used to determine whether the compound inhibits, resists, or more slowly undergoes metabolism compared to the natural PSDP. This method is performed by preparing at least one enzyme which metabolizes PSDPs, contacting the compound with the enzyme preparation, and determining whether the compound inhibits, resists, or more slowly undergoes metabolism by the enzyme. Cells having a PSDP recognition site, such as polymorphonuclear neutrophils, peripheral blood monocytes, and differentiated HL-60 cells are among the appropriate sources for the enzyme preparation. The PSDP recognition site may exist naturally, or be induced artificially, by a disease state, or by an injury. A non-limiting example of artificially-induced PSDP recognition sites is the induction of such sites in differentiated HL-60 cells in culture.

PSDP analogs can also be screened for binding activity with a PSDP receptor recognition site, for example by contacting the compound with a receptor recognition site and determining whether and to what degree the compound binds. Examples of kinetic binding assays include homologous displacement, competitive binding, isotherm, and equilibrium binding assays.

The receptor recognition site may normally exist or it may be induced by a disease state, by an injury, or by artificial means. For example, retinoic acid, PMA, or DMSO may be used to induce differentiation in HL-60 cells. Differentiated HL-60 cells express PSDP-specific receptor recognition sites. Examples of other cells which may be screened for PSDP specificity include PMN, epithelial cells, and peripheral blood monocytes or vascular endothelial cells.

Selection of competitive ligands will depend upon the nature of the recognition site, the structure of the natural substrate, any structural or functional analogs of the natural substrate known in the art, and other factors considered by a skilled artisan in making such a determination. Such ligands also include known receptor antagonists. The compounds of this invention may be radiolabelled with isotopes including $^2H$, $^3H$, $^{13}C$, and $^{14}C$ by standard techniques known in the art of radiochemistry or synthetic chemistry.

In one embodiment, the present invention pertains to a method of screening for a compound which modulates phospholipase D (PLD) activity. The method includes combining the compound with phospholipase D (PLD), thereby forming a mixture and treating the mixture with phosphatidylcholine, such that a cleavage reaction between phosphatidylcholine and PLD can occur, resulting in generation of phosphatidic acid and choline. The amount of choline produced is evaluated such that a compound which modulates PLD activity is determined. Preferably, the compound is PSDP or a PSDP analog which decreases cleavage of phosphatidylcholine by PLD. Alternatively, the compound increases cleavage of phosphatidyl choline by PLD. includes an oxidation step of choline. The method can further include an oxidation step of choline, e.g., the oxidation mixture can be peroxidase, 4-aminoantipyrine, phenol and choline oxidase.

The terms "modulates" and "modulating" are intended to include inhibition, eradication, or prevention of an activity, e.g., intracellular signaling or production of an undesired chemical species. In some instances the terms "modulates" and "modulating" also includes the increase of an activity where beneficial to the physiology of the cell or tissue environment.

In another embodiment, the present invention pertains to a method of screening for a compound which modulates intracellular signaling. The method includes combining a compound with phospholipase D (PLD), thereby forming a mixture and treating the mixture with phosphatidylcholine, such that a cleavage reaction between phosphatidylcholine and PLD occurs, resulting in generation of phosphatidic acid and choline. The amount of choline produced is evaluated, such that a compound which modulates intracellular signaling is determined. Preferably, the compound is PSDP or a PSDP analog which decreases cleavage of phosphatidylcholine by PLD. Alternatively, the compound increases cleavage of phosphatidyl choline by PLD. The method can include an oxidation step of choline. The method can further include an oxidation step of choline, e.g., the oxidation mixture can be peroxidase, 4-aminoantipyrine, phenol and choline oxidase. Alternatively, methods of detection include those recognized by those skilled in the art and include, for example, TLC, HPLC, MS, GC, etc.

In still another embodiment, the invention pertains to a method of screening for a compound which associates with protein phosphate-sensing domains. The method includes contacting a Gst-Grb2 fusion protein complexed to a support with a labeled lipid compound, e.g., a radiolabeled PSDP or PSDP analog, with and evaluating the amount of labeled compound associated with the protein. The method can further include treating the labeled lipid compound associated with a competing compound and evaluating the amount of labeled compound removed from the Gst-Grb2 fusion protein. Preferably, the support is agarose. Competing compounds are unlabeled PSDP, PSDP analogs, or delipidated albumin.

The term "competing compound" is intended to include those compounds which can displace labeled compounds, such as radiolabeled PSDP, which are associated with the Gst-Grb2 fusion protein.

The terms "associates" and "associated with" are intended to include those physical interactions between a lipid and a protein, e.g., hydrophobic, hydrophilic, ionic, hydrogen bonding, dipole interactions, etc. which cause the lipid and protein to bind to each other, e.g., absorption or adsorption.

In yet another embodiment, the invention pertains to a method of screening for a compound which modulates the production of inositol triphosphate. The method includes treating polymorphoneutrophils with a stimulation agent, e.g., fMLP, causing activation of cell, thereby producing inositol phosphate and treating the activated cells with a modulating compound. The effect of the modulating compound, e.g., PSDP or a PSDP analog, is measured on production of the inositol phosphate. A preferred stimulation agent is fMLP. Other stimulating agents include leukotrienes, cytokines, granulocyte monocyte colony stimulating factors (gm-csf), lipopolysaccharides and CFA. A preferred modulating compound is PSDP, e.g., an inhibititory compound.

In still another embodiment, the invention pertains to a method of screening for a compound which modulates neutrophil activation. The method includes treating neutrophils with a stimulation agent, e.g., fMLP, causing activation of the neutrophils, thereby producing inositol phosphate and treating the activated neutrophils with a modulating compound. The effect of the modulating compound, e.g., PSDP or a PSDP anlog, is measured on production of the inositol phosphate. A preferred stimulation agent is fMLP. A preferred modulating compound is PSDP, e.g., an inhibititory compound.

V. Experimentals

Inositol Trisphosphate Assay

Amersham's D-myo-inositol 1,4,5-trisphosphate ($IP_3$) [$^3$H] assay was used for this procedure (Amersham code TRK 1000, including product assay, the contents of which are incorporated herein by reference). The assay is based on procedures developed by Takata S. et al. J. Clin. Invest. 93:499 (1994) and Dillon S. B. et al. J. Biol. Chem. 262:11546 (1987), the contents of which are incorporated herein by reference in their entirety.

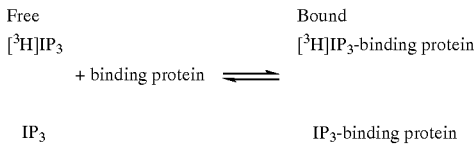

Solutions of 250 µl of PMN (10×10$^6$) in phosphate buffered saline with 1 mM $CaCl_2$ and $MgCl_2$ (physiological pH) were placed into 1.5 ml Eppendorf tubes and warmed at 37° C. for 3 minutes. To the solutions were added 25 µl of 0.25% aqueous ethanol or a test compound in 0.25% aqueous ethanol. (Test compounds included PSDP and PSMP in concentrations between 10$^{-8}$ and 10$^{-6}$ M) The mixture was incubated for 5 minutes at 37° C. To this solution was added 25 µl of 0.25% aqueous ethanol or fMLP (10$^{-7}$ M) in 0.25 aqueous ethanol for a total solution of 300 µl. The solution was incubated for 0 to 60 seconds and the reaction was stopped with 100 µl of 10% perchloric acid (PCA) with vortexing.

The cell extract was centrifuged at 14,000 rpm for 5 minutes at 4° C. The supernatant was transferred to new tubes, to which was added ¹⁄₄₀ volume (10 µl) of 1 M HEPES (pH 7.4) and ¹⁄₂₀ volume (20 µl) of pH indicator (Fisher). The color was adjusted from pink to green with 10 N KOH for a pH between 7 and 8 (14–18 µl KOH generally). (If pH>8 5% PCA was added until pH was between 7–8). The mixture was chilled at 0° C. for 20 minutes.

The supernatants were centrifuged at 14,000 rpm for 5 minutes at 4° C. To the supernatants were added 50 µl of buffer (0.1 M Tris buffer (pH 9.0) containing 4 mM EDTA and 4 mg/ml BSA) and 50 µl tracer radiolabel (D-myo-[$^3$H] inositol 1,4,5-trisphosphate, 3 nmol in water) per tube. To this was added 50 µl standards (D-myo-inositol 1,4,5-trisphosphate, 3 nmol in water) or experimental samples (compounds) per tube. To this was added 50 µl binding protein ($IP_3$ binding protein). The solution was chilled at 0° C. for 15 minutes.

The samples were centrifuged at 10,000 rpm for 5 minutes at 4° C. to separate bound from unbound $IP_3$. The supernatant was discarded by gentle vacuum and the resultant pellet was resuspended in 100 µl water with vortexing. The dissolved pellet was subjected to scintillation counting and rates of reaction were determined (See FIGS. 6 and 7).

PSDP Equilibrium Binding Assay to GST-GRB2

GST-GRB2 complexed to agarose beads was purchased from Upstate Biotechnology, Inc. Microcentrifuge spin nylon filters (0.2 µm) were purchased from PGC Scientific).

To 100 µl of 0.9% NaCl was added 2 µg GST-GRB2 with 0–100 µg compound (e.g., delipidated human serum albumin, SH3-bearing SOS peptide or unlabeled PSDP) to be tested. The samples were prepared directly in the top of PGC spin filter tubes.

To the solution was added radiolabeled-PSDP in 1 µl ethanol. The mixture was vortexed and incubated at 37° C. for 30 minutes. After the incubation period, the sample was centrifuged at 2000 rpm at 25° C. for 3 minutes. The top of the tube was rinsed with 200 µl of chloroform:methanol 2:1 (v/v) (the sample should not be vortexed at this stage). This sample was centrifuged at 2000 rpm at 25° C. for 3 minutes. The filter was removed, placed in a scintillation vial and the amount of radioactivity bound to the trapped agarose complex (i.e., bound material) was determined.

1 ml of $CHCl_3$:MeOH (2:1) was added to the filtrate (a clear interface should be evident). The upper phase was removed and discarded and the lower phase was brought to dryness under a gentle stream of nitrogen. The concentrate was resuspended in 40 µl $CHCl_3$:MeOH (2:1 v/v). At this stage, dependent upon the amount of radioactivity present, the radioactivity of the sample was determined either in scintillation fluid or by phosphoimage after TLC. When necessary, TLC was performed in $CHCl_3$:MeOH:water 65:25:4 (v/v/v) at 25° C.×50 minutes. The phosphoimage was analyzed by densitometry (FIG. 8).

Bound material is reflected in the filtrate by loss of radioactivity when radiolabeled material is incubated in the presence of the GRB2 complex compared to the absence of the agarose complex. The difference is defined as 100% binding so that comparisons can be made to unknown compounds tested in parallel.

VII. Equivalents

Those skilled in the art will recognize, or be able to ascertain using no more than routine experimentation, many equivalents to specific embodiments of the invention described specifically herein. Such equivalents are intended to be encompassed in the scope of the following claims. The contents of all references and issued patents cited throughout all portions of this application including the background are expressly incorporated by reference.

What is claimed is:

1. A method of screening for a compound which modulates the production of inositol trisphosphate, comprising the steps of:
   a) contacting polymorphonuclear leukocytes with a stimulation agent, causing activation of a cell, thereby producing inositol trisphosphate;
   b) contacting said activated cell with a modulating compound; and
   c) determining the effect of said modulating compound on production of said inositol trisphosphate.

2. The method of claim 1, wherein said stimulation agent is formyl-methionyl-leucyl-phenylalanine, a leukotriene, a cytokine, a granulocyte monocyte colony stimulating factor, a lipopolysaccharide or complete Fruends adjuvent.

3. The method of claim 1, wherein said modulating compound is presqualene diphosphate.

4. The method of claim 1, wherein said modulating compound is a presqualene diphosphate analog.

5. The method of claim 1, further including the step of contacting a radiolabel to said inositol trisphosphate of step c).

6. The method of claim 1, wherein production of phospholipase C activity is determined.

7. A method of screening for a compound which modulates neutrophil activation, comprising the steps of:
   a) contacting neutrophils with a stimulation agent, causing activation of said neutrophils, thereby producing inositol phosphate;
   b) contacting said activated neutrophils with a modulating compound; and
   c) determining the effect of said modulating compound on production of said inositol phosphate.

8. The method of claim 7, wherein said stimulation agent is formyl-methionyl-leucyl-phenylalanine, a leukotriene, a cytokine, a granulocyte monocyte cloning stimulating factor, a lipopolysaccharide or complete Freunds adjuvant.

9. The method of claim 7, wherein said modulating compound is presqualene diphosphate.

10. The method of claim 7, wherein said modulating compound is a presqualene diphosphate analog.

11. The method of claim 7, further including the step of contacting a radiolabel to said inositol phosphate of step c).

12. The method of claim 7, wherein production of phospholipase C activity is determined.

* * * * *